US005663060A

United States Patent [19]

Lollar et al.

[11] Patent Number: 5,663,060
[45] Date of Patent: Sep. 2, 1997

[54] HYBRID HUMAN/ANIMAL FACTOR VIII

[75] Inventors: John S. Lollar, Decatur; Marschall S. Runge, Atlanta, both of Ga.

[73] Assignee: Emory University, Atlanta, Ga.

[21] Appl. No.: 212,133

[22] Filed: Mar. 11, 1994

Related U.S. Application Data

[63] Continuation-in-part of Ser. No. 864,004, Apr. 7, 1992, Pat. No. 5,364,771.

[51] Int. Cl.$^6$ .................... C07K 14/755; C07K 14/745; C12N 15/12; A61K 38/37
[52] U.S. Cl. ................. 435/69.6; 435/172.3; 530/383; 930/100
[58] Field of Search .................... 435/69.6, 172.3, 435/320.1, 240.2, 252.3; 530/383; 514/12; 930/100

[56] References Cited

U.S. PATENT DOCUMENTS

| Re. 32,011 | 10/1985 | Zimmerman et al. | 530/383 |
|---|---|---|---|
| 4,554,101 | 11/1985 | Hopp | 530/324 |
| 4,757,006 | 7/1988 | Toole et al. | 435/69.6 |
| 4,868,112 | 9/1989 | Toole, Jr. | 514/8 |
| 4,965,199 | 10/1990 | Capon et al. | 435/69.6 |
| 4,970,300 | 11/1990 | Fulton et al. | 530/383 |
| 4,980,456 | 12/1990 | Scandella et al. | 530/383 |
| 5,004,803 | 4/1991 | Kaufman et al. | 530/383 |
| 5,246,850 | 9/1993 | Bennett et al. | 435/212 |
| 5,317,010 | 5/1994 | Pang et al. | 514/12 |
| 5,338,546 | 8/1994 | Bennett et al. | 424/94.64 |
| 5,563,045 | 10/1996 | Pittman | 435/69.6 |

FOREIGN PATENT DOCUMENTS

| WO 91/09122 | 6/1991 | WIPO. |
|---|---|---|
| WO 92/16557 | 10/1992 | WIPO. |
| WO 93/20093 | 10/1993 | WIPO. |

OTHER PUBLICATIONS

Elder, B. et al. Genomics 16:374–379 (1993).
Lollar, P. et al. J. Biol. Chem. 266(19):12481–12486 (1991).
Arai, M., et al., "Molecular basis of factor VIII inhibition by human antibodies," 83 *J. Clin. Invest.* 1978–1984 (1989).
Burke, R.L., et al., "The functional domains of coagulation factor VIII:C," 261 *J. Biol. Chem.* 12574–12578 (1986).
Eaton, D., et al., "Proteolytic processing of human factor VIII. Correlation of specific cleavages by thrombin, factor Xa, and activated protein C with activation and inactivation of factor VIII coagulant activity," 25 *Biochem.* 505–512 (1986).
Eaton, D.L., et al., "Construction and characterization of an active factor VIII variant lacking the central one-third of the molecule," 25 *Biochem.* 8343–8347 (1986).
Eaton, D.L., et al., "Characterization of recombinant human factor VIII," 262 *J. of Biol. Chem.* 3285–3290 (1987).
Fass, D.N., et al., "Monoclonal antibodies to porcine factor VIII coagulant and their use in the isolation of active coagulant protein," 59 *Blood* 594–600 (1982).

Fay, P.J., et al., "The size of human factor VIII heterodimers and the effects produced by thrombin," 871 *Biochimica et Biophysica Acta* 268–278 (1986).
Fay, P.J., "Subunit structure of thrombin-activated human factor VIII," 952 *Biochimica et Biophysica Acta* 181–190 (1987).
Fay, P.J., "Reconstitution of human factor VIII from isolated subunits," 262 *Arch. Biochem. Biophys.* 525–531 (1988).
Fay, P.J., et al., "Topography of the human factor VIII—von Willebrand factor complex," 265 *J. Biol. Chem.* 6197–6202 (1990).
Fay, P.J., "von Willebrand factor mediates protection of factor VIII from activated protein C–catalyzed inactivation," 266 *J. Biol. Chem.* 2172–2177 (1991).
Fay, P.J., et al., "Human factor VIII subunit structure," 266 *J. Biol. Chem.* 1–6 (1991).
Fulcher, C.A., and T.S. Zimmerman, "Characterization of the human factor VIII procoagulant protein with a heterologous precipitating antibody," 79 *Proc. Nat'l. Acad. Sci. U.S.A.* 1648–1652 (1982).
Fulcher, C.A., et al., "Human factor VIII procoagulant protein," 76 *J. Clin. Invest.* 117–124 (1985).
Gitschier, J., et al., "Characterization of the human factor VIII gene," 312 *Nature* 326–330 (1984).
Hill–Eubanks, D.C., and P. Lollar, "von Willebrand factor is a cofactor for thrombin–catalyzed cleavage of the factor VIII light chain," 265 *J. Biol. Chem.* 17854–17858 (1990).
Kaufman, R.J., et al., "Synthesis, processing, and secretion of recombinant human factor VIII expressed in mammalian cells," 263 *J. Biol. Chem.* 6352–6362 (1988).
Kaufman, R.J., et al., "Effect of von Willebrand factor coexpression on the synthesis and secretion of factor VIII in Chinese hamster ovary cells," 9 *Molec. Cell. Biol.* 1233–1242 (1989).
Koedam, J.A., et al., "The effect of von Willebrand factor on activation of factor VIII by factor Xa," 189 *Eur. J. Biochem.* 229–234 (1990).

(List continued on next page.)

*Primary Examiner*—Dian C. Jacobson
*Attorney, Agent, or Firm*—Greenlee, Winner and Sullivan P.C.

[57] ABSTRACT

A hybrid human/animal coagulation factor VIII is produced by isolation and recombination of human and other non-human mammalian factor VIII subunits or domains, or by genetic engineering of the human and animal factor VIII genes. Subunits or domains of factor VIII that have been purified from human or animal plasma are isolated, and hybrid human/animal factor VIII is produced by (1) mixing either animal heavy chain subunits with human light chain subunits or by mixing human heavy chain subunits with animal light chain subunits, thereby producing human light chain/animal heavy chain and human heavy chain/animal light chain hybrid molecules; or by (2) mixing one or more domains of one species with one or more domains of the other species. These hybrid molecules are isolated by ion exchange chromatography. Alternatively, recombinant DNA methods are used to change elements of animal factor VIII or human factor VIII to the corresponding elements of human factor VIII or animal factor VIII, respectively, to produce hybrid human/animal factor VIII.

23 Claims, 4 Drawing Sheets

OTHER PUBLICATIONS

Kohn, D.B., and P.W. Kantoff, "Potential applications of gene therapy," 29 *Transfusion* 812–820 (1989).

Leyte, A., et al., "Sulfation of Tyr$^{1680}$ of human blood coagulation factor VIII is essential for the interaction of factor VIII with von Willebrand factor," 266 *J. Biol. Chem.* 740–746 (1991).

Lollar, P., et al., "Activation of porcine factor VIII:C by thrombin and factor Xa," 24 *Biochemistry* 8056–8064 (1985).

Lollar, P. (J.S.), et al., "Association of the factor VIII light chain with von Willebrand factor," 263 *J. Biol. Chem.* 10451 (1988).

Lollar, P.(J.S.), et al., "Molecular characterization of commercial porcine factor VIII concentrate," 71 *Blood* 137–143 (1988).

Lollar, P.(J.S.), and C.G. Parker, "Subunit structure of thrombin–activated porcine factor VIII," 28 *Biochemistry* 666–674 (1989).

Lollar, P., and C.G. Parker, "pH–dependent denaturation of thrombin–activated porcine factor VIII," 265 *J. Biol. Chem.* 1688–1692 (1990).

Lollar, P., "The association of factor VIII with von Willebrand factor," 66 *Mayo Clin. Proc.* 542–534 (1991).

Lollar, P., and E.T. Parker, "Structural basis for the decreased procoagulent activity of human factor VIII compared to the porcine homolog," 266 *J. Biol. Chem.* 12481–12486 (1991).

Mosesson, M.W., et al., "Structural model of porcine factor VIII and factor VIIIa molecules based on scanning transmission electron microscope (STEM) images and STEM mass analysis," 85 *J. Clin. Invest.* 1983–1990 (1990).

Naylor, J.A., et al., "Detection of three novel mutations in two haemophilia A patients by rapid screening of whole essential region of factor VIII gene," 337 *The Lancet* 635–639 (1991).

Pittman, D.D., and R.J. Kaufman, "Proteolytic requirements for thrombin activation of anti–hemophilic factor (factor VIII)," 85 *Proc. Nat'l. Acad. Sci. U.S.A.* 2429–2433 (1988).

Roberts, H.R., and M.R. Jones, "Hemophilia and related conditions—Congenital deficiencies of prothrombin (factor IM, factor V, and factors VII to XII," Ch. 153, 1453–1474, 1460, in *Hematology*, Williams, W.J., et al., ed., 1990.

Toole, J.J., et al., "Molecular cloning of a cDNA encoding human antihaemophilic factor," 312 *Nature* 342–347 (1984).

Toole, J.J., et al., "A large region (≈95 kDa) of human factor VIII is dispensable for in vitro procoagulent activity," 83 *Proc. Nat'l. Acad. Sci. U.S.A.* 5939–5942 (1986).

Vehar, G.A., and E.W. Davie, "Preparation and properties of bovine factor VIII (antihemophilic factor)," 19 *Biochem.* 401–410 (1980).

Vehar, G.A., et al., "Structure of human factor VIII," 312 *Nature* 337–342 (1984).

Walker, F.J., et al., "Identification of the binding site for activated protein C on the light chain of factors V and VIII," 265 *J. Biol. Chem.* 1484–1489 (1990).

Ware, J., et al., "Localization of a factor VIII–inhibiting antibody epitope to a region between residues 338 and 362 of factor VIII heavy chain," 85 *Proc. Natl. Acad. Sci. USA* 3165–3169 (1988).

Wood, W.I., et al., "Expression of active human factor VIII from recombinant DNA clones," 312 *Nature* 330–337 (1984).

Scandella, D., et al., "Localization of Epitopes for Human Factor VIII Inhibitor Antibodies by Immunoblotting and Antibody Neutralization," 111 (25) *Chem. Abst.* 570, Abst. 230240 (Dec. 18, 1989).

Scandella, D., et al., "Localization of Epitopes for Human Factor VIII Inhibitor Antibodies by Immunoblotting and Antibody Neutralization," 82 (6) *Blood* 1767–1775 (1993).

Scandella, D. et al., "A Recombinant Factor VIII A2 Domain Polypeptide Quantitatively Neutralizes Human Inhibitor Antibodies that Bind to A2," 121 (19) *Chem. Abst.* 782, Abst. 268801 (Dec. 20, 1993).

Scandella, D. et al., "A Recombinant Factor VIII A2 Domain Polypeptide Quantitatively Neutralizes Human Inhibitor Antibodies that Bind to A2," 74 (5) *Blood* 1618–1626 (1989).

Brinkhous, K.M., et al., "Purified Human Factor VIII Procoagulant Protein: Comparative Hemostatic Resonce After Infusions into Hemophilic and von Willebrand Disease Dogs", *Proc. Natl. Acad. Sci. U.S.A.*, 82:8752–8755 (1985).

Hoeben, R.C., "Expression of Functional Factor VIII in Primary Human Skin Fibroblasts After Retrovirus–mediated Gene Transfer", *J. Biol. Chem.*, 265(13):7318–7323 (1990).

Hoeben, R.C., et al., "Toward Gene Therapy for Hemophilia A: Long–Term Persistence for Factor VIII–Secreting Fibroblasts After Transplantation into Immunodeficient Mice", *Human Gene Therapy*, 4(2):179–186 (1993).

Horton, R.M., et al., "Gene Splicing by Overlap Extension", *Meth. Enzymol.*, 217:270 (1993).

Levinson, B., et al., "Sequence of the Human Factor VII–I–Associated Gene is Conserved in Mouse", *Genomics*, 13:862–865 (1992).

Lollar, P., et al., "Inhibition of Human Factor VIIIa by Anti–A2 Subunit Antibodies", *Blood*, 82:Abstract No. 230 (1993).

Lollar, P., et al., "Coagulant Properties of Hybrid Human–Porcine Factor VIII Molecules", *J. Biol. Chem.*, 267:23652–23657 (1992).

Lubin, I.M., et al., "Elimination of a Major Inhibitor Epitope in Factor VIII", *J. Biol. Chem.*, 269(12):8639–8641 (1994).

Lubin, L.M., et al., "Expression of a Recombinant Hybrid Human/Porcine Factor VIII Molecule with Elimination of Reactivity Toward an Inhibitory Anti–Human A2 Domain Antibody", *Blood*, 82:Abstract 229 (1993).

Lusher, J.M., et al., "Recombinant Factor VIII for the Treatment of Previously Untreated Patients with hemophilia A", *New. Engl. J. Med.*, 328(7):453–459 (1993).

Pittman, D.D., et al., "A2 Domain of Human Recombinant–Derived Factor VIII is Required for Procoagulant Activity but not for Thrombin Cleavage", *Blood*, 79(2):389–397 (1992).

Rebemtulla, A., "Improved Procoagulant Activity of Human Factor VIII Molecules Containing Portions of Porcine Sequence", *Blood*, 82:Abstract 1339 (1993).

Sarkar, G., et al., "Access to a Messenger RNA Sequence or its Protein Product is not Limited by Tissue or Species Specificity", *Science*, 244:331–334 (1989).

Shima, M., et al., "Factor VIII Neutralizing Monoclonal Antibody and a Human Inhibitor Alloantibody Recognizing Epitopes in the C2 Domain Inhibit Binding to von Willebrand Factor and to Phosphatidyl Serine", *Thromb. Haemostas.*, 69:240–246 (1993).

```
        373
Pig     SVAKKHPKTWVHYISAEEEDWDYAPAVPSPDRSYKSLYLNSGPQRIGRKYKKARFVAYT ...........   432
Hum     SVAKKHPKTWVHYIAAEEEDWDYAPLVLAPDDRSYKSQYLNNGPQRIGRKYKKVRFMAYT ...........   432
        *****  *****  *** *****      * *****  ** ******   ***  * ****
Mou     SVAKKYPKTWIHYISAEEEDWDYAPSVPTSDNGSYKSQYLSNGPHRIGRKYKKVRFIAYT ...........   432

2
Pig     DVTFKTRKAIPYESGILGPLLYGEVGDTLLIIFKNKASRPYNIYPHGITDVSALHPGRLL ...........   492
Hum     DETFKTREAIQHESGILGPLLYGEVGDTLLIIFKNQASRPYNIYPHGITDVRPLYSRRLP ...........   492
        * ***** ** ************************ ************** *    * 
Mou     DETFKTRETIQHESGLLGPLLYGEVGDTLLIIFKNQASRPYNIYPHGITDVSPLHARRLP ...........   492

Pig     KGWKHLKDMPILPGETFKYKWTVTVEDGPTKSDPRCLTRYYSSSINLEKDLASGLIGPLL ...........   552
Hum     KGVKHLKDFPILPGEIFKYKWTVTVEDGPTKSDPRCLTRYYSSFVNMERDLASGLIGPLL ...........   552
        ** ***** ****** ************************** *  * **********
Mou     RGIKHVKDLPIHPGEIFKYKWTVTVEDGPTKSDPRCLTRYYSSFINPERDLASGLIGPLL ...........   552

5
Pig     ICYKESVDQRGNQMMSDKRNVILFSVFDENQSWYLAENIQRFLPNPDGLQPQDPEFQASN ...........   612
Hum     ICYKESVDQRGNQIMSDKRNVILFSVFDENRSWYLTENIQRFLPNPAGVQLEDPEFQASN ...........   612
        ************* **************** **** ********* *  * *******
Mou     ICYKESVDQRGNQMMSDKRNVILFSIFDENQSWYITENMQRFLPNAAKTQPQDPGFQASN ...........   612
```

FIG. 2A

```
Pig  IMHSINGYVFDSLQLSVCLHEVAYWYILSVGAQTDFLSVFFSGYTFKHKMVYEDTLTLFP         672
Hum  IMHSINGYVFDSLQLSVCLHEVAYWYILSIGAQTDFLSVFFSGYTFKHKMVYEDTLTLFP         672
     **** * ******************** **************************
Mou  IMHSINGYVFDSLELTVCLHEVAYWHILSVGAQTDFLSIFFSGYTFKHKMVYEDTLTLFP         672

6                                7
Pig  FSGETVFMSMENPGLWVLGCHNSDLRNRGMTALLKVYSCDRDIGDYYDNTYEDIPGFLLS         732
Hum  FSGETVFMSMENPGLWILGCHNSDFRNRGMTALLKVSSCDKNTGDYYEDSYEDISAYLLS         732
     ******* ******* *******  * **  * ****  **** * *****  *
Mou  FSGETVFMSMENPGLWVLGCHNSDFRKRGMTALLKVSSCDKSTSDYYEEIYEDIPTQLVN         732

Pig  GKNVIEPR                                                            740
Hum  KNNAIEPR                                                            740
     * * ****
Mou  ENNVIDPR                                                            740
```

FIG. 2B

HYBRID HUMAN/ANIMAL FACTOR VIII

This application is a continuation-in-part of application Ser. No. 07/864,004, filed Apr. 7, 1992, now U.S. Pat. No. 5,364,777.

The government has rights in this invention arising from National Institutes of Health Grant No. HL 40921 that partially funded the research leading to this invention.

BACKGROUND OF THE INVENTION

This invention relates generally to a hybrid factor VIII having human and animal factor VIII amino acid sequence and methods of preparation and use thereof.

This invention is a continuation-in-part of U.S. Ser. No. 07/864,004 entitled "Hybrid Human/Porcine Factor VIII" filed Apr. 7, 1992, by John S. Lollar and Marschall S. Runge.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps. In its active form, the protein factor VIII is a cofactor that is required for the activation of factor X by the protease, activated factor IX.

Factor VIII or antihemophilic factor was noticed in plasma and named in the 1930s. In the 1940s, a deficiency in factor VIII was associated with the clotting disorder hemophilia A. Factor VIII was found to be X-linked and was hypothesized to be a protein. Work involving bovine, human, and porcine plasma identified factor VIII as a protein in the 1980s, though its definitive cellular source remains uncertain.

Precisely how factor VIII functions in blood coagulation is unknown. It is known that factor VIII is activated to factor VIIIa proteolytically by thrombin or factor Xa. In combination with calcium and phospholipid, factor VIIIa makes factor IXa a more efficient activator of factor X by an unknown mechanism.

People deficient in factor VIII or having antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII, clinical trials for which are underway. Additionally, a preparation of partially-purified porcine factor VIII is available to treat patients with inhibitors to human factor VIII, i.e., those who have circulating antibody molecules that bind and neutralize human factor VIII.

Hemophiliacs require daily replacement of factor VIII to prevent the deforming hemophilic arthropathy that occurs after many years of recurrent hemorrhages into the joints. However, supplies of factor VIII concentrates have never been plentiful enough for treating hemophiliacs adequately because of problems in commercial production and therapeutic use. For example, the commonly used plasma-derived is difficult to isolate and purify, is immunogenic, and requires treatment to remove the risk of infectivity from AIDS and hepatitis viruses. Recombinant human factor VIII may lessen the latter two problems. Porcine factor VIII may also present an alternative, since human factor VIII is unstable at physiologic concentrations and pH, is present in blood at an extremely low concentration (0.2 μg/ml plasma), and its specific clotting activity is low, compared with porcine factor VIII.

Since many inhibitors of human factor VIII react less strongly with porcine factor VIII, porcine factor VIII is currently used to correct factor VIII deficiency in patients under conditions in which they do not respond to infusions of human factor VIII. A limitation of porcine factor VIII is the development of inhibitory antibodies to it after one or more infusions.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to produce inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors of human factor VIII.

It is a further object of the present invention to provide methods for treatment of hemophiliacs.

It is another object of the present invention to provide a factor VIII with an increased efficacy in factor VIII clotting assays.

It is still another object of the present invention to provide a factor VIII that is stable at a selected pH and physiologic concentration.

It is yet another object of the present invention to provide a diagnostic assay for detecting the presence of inhibitors to factor VIII.

SUMMARY OF THE INVENTION

A hybrid coagulation factor VIII having human factor VIII amino acid sequence and factor VIII amino acid sequence of pig or another non-human mammal (referred to herein as "animal") is produced by isolation and recombination of human and animal factor VIII subunits or domains; or by genetic engineering of the human and animal factor VIII genes.

In the preferred embodiment, recombinant DNA methods are used to substitute elements of animal factor VIII for the corresponding elements of human factor VIII, resulting in hybrid human/animal factor VIII molecules.

In another embodiment, subunits of factor VIII are isolated and purified from human or animal plasma, and hybrid human/animal factor VIII is produced either by mixture of animal heavy chain subunits with human light chain subunits or by mixture of human heavy chain subunits with animal light chain subunits, thereby producing human light chain/animal heavy chain and human heavy chain/animal light chain hybrid molecules. These hybrid molecules are isolated by ion exchange chromatography.

Alternatively, one or more domains or partial domains of factor VIII are isolated and purified from human or animal plasma, and hybrid human/animal factor VIII is produced by mixture of domains or partial domains from one species with domains or partial domains of the second species. Hybrid molecules can be isolated by ion exchange chromatography.

Methods for preparing highly purified hybrid human/animal factor VIII are described having the steps of: (a) isolation of subunits of plasma-derived human factor VIII and subunits of plasma-derived animal factor VIII, followed by reconstitution of coagulant activity by mixture of human and animal subunits, followed by isolation of hybrid human/animal factor VIII by ion exchange chromatography; (b) isolation of domains or partial domains of plasma-derived human factor VIII and domains or partial domains of plasma-derived animal factor VIII, followed by reconstitution of coagulant activity by mixture of human and animal domains, followed by isolation of hybrid human/animal factor VIII by ion exchange chromatography; (c) construction of domains or partial domains of animal factor VIII by recombinant DNA technology, followed by exchanging of domains of animal and human factor VIII to produce hybrid human/animal factor VIII with coagulant activity; or (d) creation of hybrid human/animal factor VIII by replacement of specific amino acid residues of human factor VIII with the homologous animal factor VIII amino acid residues by site-directed mutagenesis.

Some species of hybrid human/porcine and other human/non-human mammalian factor VIII have specific activity greater than human factor VIII and equal to or slightly higher than porcine factor VIII.

BRIEF DESCRIPTION OF THE DRAWINGS

FIG. 2A and 2B is an amino acid sequence alignment of human, mouse, and porcine factor VIII A2 domains, in which residue numbering begins at position 373 with respect to the full length sequence of human factor VIII (Sequence ID No. 2).

DETAILED DESCRIPTION OF THE INVENTION

Definitions

Figure 1:
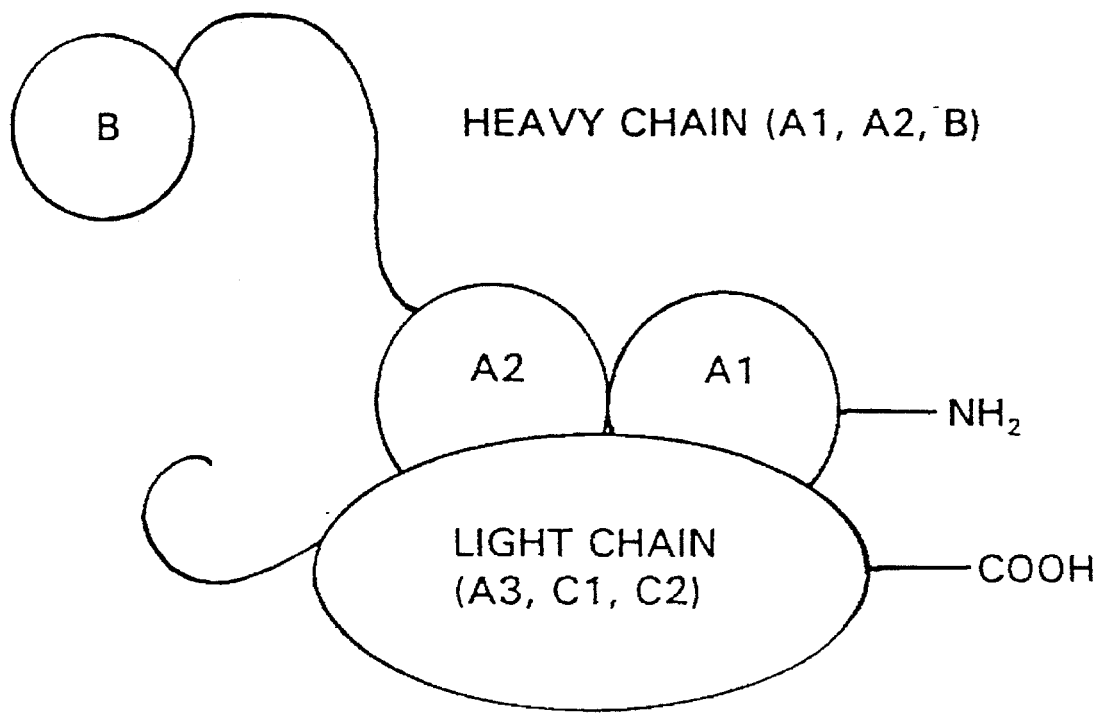
FIG. 1 (Prior Art) is a diagrammatic representation of a factor VIII molecule showing the subunits (heavy and light chains) and the domains.

As used herein, "hybrid human/animal factor VIII" denotes any functional factor VIII protein molecule with sequence derived from both human and porcine or other non-human mammalian factor VIII. As used herein, "mammalian factor VIII" includes factor VIII with amino acid sequence derived from any non-human mammal, unless otherwise specified. "Animal", as used herein, refers to pig and other non-human mammals. Hybrid human/porcine factor VIII has activity in a human factor VIII assay. This activity, as well as that of other human/non-porcine mammalian factor VIII, may exceed that of either plasma-derived or recombinant human factor VIII. In some embodiments, this hybrid human/porcine or other human/non-porcine mammalian factor VIII is not cross-reactive with all human factor VIII antibodies.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed.

A "hybrid factor VIII" or "hybrid protein," as used herein, is a factor VIII protein in which the amino acid sequence is derived in part from human and in part from animal origin. This hybrid factor VIII can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; or (4) by changing one or more amino acid residue(s) in human factor VIII to the residue(s) in the corresponding animal sequence. A fusion protein is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid protein described in this application.

The human factor VIII cDNA nucleotide sequence is shown in Sequence ID No. 1. The human factor VIII predicted amino acid sequence is shown in Sequence ID No. 2. In a factor VIII molecule, a "domain" as used herein is a continuous sequence of amino acids that are defined by internal amino acid sequence homology and sites of proteolytic cleavage by thrombin. Unless otherwise specified, factor VIII domains include the following amino acid residues, when the sequences are aligned with the human amino acid sequence (Sequence ID No. 2): A1, residues 1–372; A2, residues 373–740; B, residues 741–1648; A3, residues 1690–2032; C1, residues 2033–2182; C2, residues 2183–2332. The A3-C1-C2 sequence includes residues 1690–2332. The remaining sequence, residues 1649–1689, is usually referred to as the factor VIII light chain activation peptide. A "partial domain" as used herein is a continuous sequence of amino acids containing part of a domain.

As used herein, a "hybrid human/animal factor VIII equivalent" is an active factor VIII molecule wherein (1) a sequence of one or more amino acid residues in the human, animal, or hybrid human/animal factor VIII that forms an epitope which is immunoreactive with endogenous factor VIII inhibitory antibodies is substituted with a sequence of one or more amino acid residues, having no known homology to human or animal factor VIII sequence, that does not form an epitope immunoreactive with endogenous factor VIII inhibitory antibodies; and/or (2) a sequence of one or more amino acid residues in the human, animal, or hybrid human/animal factor VIII that is critical to coagulant activity is substituted with a sequence of one or more amino acid residues, having no known homology to human or animal factor VIII sequence that also has coagulant activity. The resulting hybrid human/animal factor VIII equivalent molecule has less reactivity with factor VIII inhibitory antibodies than the unsubstituted human factor VIII and has coagulant activity.

"Factor VIII deficiency," as used herein, includes deficiency in clotting activity caused by production of a defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

"Subunits" of human or animal factor VIII, as used herein, are the heavy and light chains of the protein. The heavy chain of factor VIII contains three "domains," A1, A2, and B. The light chain of factor VIII also contains three "domains," A3, C1, and C2.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, however, the hybrid human\animal DNA and protein expressed therefrom, in whole or in part, can be substituted for the corresponding reagents in the otherwise known assays, whereby the modified assays may be used to detect and/or quantify antibodies to factor VIII. It is the use of these reagents, the hybrid human/animal DNA and protein expressed therefrom, that permits modification of known assays for detection of antibodies to human or animal factor VIII or to hybrid human/animal factor VIII. Such assays include, but are not limited to ELISAs, immunodiffusion assays, and immunoblots. Suitable methods for practicing any of these assays are known to those of skill in the art. As used herein, the hybrid human/animal factor VIII or portion thereof that includes at least one epitope of the protein, can be used as the diagnostic reagent.

The terms "epitope", "antigenic site", and "antigenic determinant", as used herein, are used synonymously and are defined as a portion of the hybrid human/animal factor VIII protein that is specifically recognized by an antibody. It can consist of any number of amino acid residues and it can be dependent upon the primary, secondary, or tertiary structure of the protein. In accordance with this disclosure, a factor VIII protein that includes at least one epitope may be used as a reagent in the diagnostic assays.

General Description of Methods

Hybrid human/animal factor VIII molecules, some of which have greater activity in a standard clotting assay when compared to highly-purified human factor VIII, can be constructed as follows.

Four types of hybrid human/porcine factor VIII and the methods for preparing them are disclosed herein: those obtained (1) by substituting a porcine subunit (i.e., heavy chain or light chain) for the corresponding human subunit; (2) by substituting one or more porcine domain(s) (i.e., A1, A2, A3, B, C1, and C2) for the corresponding human domain(s); (3) by substituting part of one or more porcine domain(s) for the corresponding part of one or more domain(s) of the human domain; and (4) by substituting one or more amino acid residue(s) in human factor VIII with the residue(s) from the corresponding porcine sequence. Four types of hybrid factor VIII molecules having human factor VIII amino acid sequence and non-porcine mammalian factor VIII amino acid sequence can also be prepared by the same methods.

Hybrid human/animal factor VIII proteins listed above under groups (1)–(3) are made by isolation of subunits, domains, or parts of domains of plasma-derived factor VIII, followed by reconstitution and purification. Hybrid human/animal factor VIII proteins described under groups (3)–(4) above are made by recombinant DNA methods. The hybrid molecule may contain a greater percentage of human than animal sequence or vice versa, depending on the origin of the various regions, as described in more detail below.

It is shown below that hybrid human/porcine factor VIII consisting of porcine heavy chain/human light chain and corresponding to the first type of hybrid listed above has greater specific coagulant activity in a standard clotting assay as compared to human factor VIII. The hybrid human/animal factor VIII with coagulant activity, whether the activity is higher or lower than that of human factor VIII, can be useful in treating patients with inhibitors, since these inhibitors can react less well with hybrid human/animal factor VIII than with either human or porcine factor VIII.

Preparation of hybrid human/animal factor VIII molecules from isolated human and animal factor VIII subunits by reconstitution:

Hybrid human/animal factor VIII molecules are prepared and isolated, and their procoagulant activity is characterized. One method, modified from procedures reported by Fay, P. J., et al., 265 *J. Biol. Chem.* 6197 (1990); and Lollar, J. S., et al., 263 *J. Biol. Chem.* 10451 (1988), the teachings of each of which are incorporated herein by reference, involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, as described by Lollar, J. S., et al., 71 *Blood* 137–143 (1988), the teachings of which are incorporated herein by reference.

These methods, described in detail in the examples below, result in hybrid human light chain/porcine heavy chain molecules with greater than six times the procoagulant activity of human factor VIII. Other hybrid human/non-porcine mammalian factor VIII molecules can be prepared, isolated, and characterized for activity by the same methods.

Preparation of hybrid human/animal factor VIII molecules from isolated human and animal factor VIII domains by reconstitution:

Hybrid human/animal factor VIII molecules with domain substitutions are prepared and isolated, and their procoagulant activity is characterized. One method involves the isolation of one or more domains of human and one or more domains of animal factor VIII, followed by recombination of human and animal domains to form hybrid human/animal factor VIII with coagulant activity, as described by Lollar, P., et al., 267(33) *J. Biol. Chem.* 23652–23657 (Nov. 25, 1992), the teachings of which are incorporated herein by reference.

Plasma-derived animal and human A1/A3-C1-C2 dimers are isolated by dissociation of the A2 domain from factor VIIIa in the presence of NaOH, after which the mixture is diluted and the dimer is eluted using monoS™ HPLC (Pharmacia-LKB, Piscataway, N.J.). The A2 domain is isolated from factor VIIIa as a minor component in the monoS™ HPLC. Hybrid human/animal factor VIII molecules are reconstituted by mixing equal volumes of the A2 domain of one species and the A1/A3-C1-C2 dimer of the other species. Hybrid factor VIII with one or more domain substitutions is isolated from the mixture of unreacted dimers and A2 domains by monoS™ HPLC by procedures for the isolation of porcine factor VIII, as described by Lollar, J. S., et al., 71 *Blood* 137–143 (1988).

These methods, described in detail in the examples below, result in hybrid factor VIII molecules with procoagulant activity.

Preparation of hybrid human/animal factor VIII molecules recombinant engineering of the sequences encoding human and animal factor VIII subunits, domains, or parts of domains:

Substitution of subunits, domains, parts of domains:

The human factor VIII gene was isolated and expressed in mammalian cells, as reported by Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech), the teachings of each of which are incorporated herein by reference, and the amino acid sequence was deduced from cDNA. U.S. Pat. No. 4,965,199 to Capon et al. discloses a recombinant DNA method for producing factor VIII in mammalian host cells and purification of human factor VIII. Factor VIII expression in CHO (Chinese hamster ovary) cells and BHKC (baby hamster kidney cells) has been reported.

The cDNA sequence encoding human factor VIII and predicted amino acid sequence are shown in Sequence ID No. 1 and Sequence ID No. 2, respectively.

Recombinant hybrid human/animal factor VIII is prepared starting with human cDNA (Biogen, Inc.) encoding the factor VIII sequence corresponding to domains A1-A2-A3-C1-C2. The factor VIII encoded by this cDNA lacks the entire B domain and corresponds to amino acid residues 1–740 and 1649–2332 of single chain human factor VIII (see Sequence ID No. 2), according to the numbering system of Wood et al., 312 *Nature* 330–337 (1984), the teachings of which are incorporated herein by reference. The B domain is deleted, since it does not appear to be necessary for biological function.

Porcine factor VIII has been isolated and purified from plasma (Fass, D. N., et al., 59 *Blood* 594 (1982)). The amino acid sequence of the B and part of the A2 domains of porcine factor VIII, as reported by Toole, J. J., et al., 83 *Proc. Nat'l. Acad. Sci. U.S.A.* 5939–5942 (1986), the teachings of which are incorporated herein by reference, is shown in Sequence ID No. 3. The corresponding genomic DNA sequence is shown in Sequence ID No. 4. The coding region in the porcine nucleotide sequence begins at position 675 (GGT CTC TGG . . .) (Sequence ID No. 4), which corresponds to amino acids (Gly-Leu-Trp) (Sequence ID No. 3), the $NH_2$terminal amino acids.

Both porcine and human factor VIII are isolated from plasma as a two subunit protein. FIG. 1 (prior art) illustrates diagrammatically the subunit structure of the factor VIII molecule. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known function and can be removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII (factor VIIIa) have three subunits due to cleavage of the heavy chain between the A1 and A2 domains. This structure is designated A1/A2/A3-C1-C2. Human factor VIIIa is not stable under the conditions that stabilize porcine factor VIIIa. This is because of the weaker association of the A2 subunit of human factor VIIIa. Dissociation of the A2 subunit of human and porcine factor VIIIa is associated with loss of activity in the factor VIIIa molecule.

The complete A2 domain of porcine factor VIII cDNA (Sequence ID No. 5), homologous to residues 373–740 in Sequence ID No. 1, in mature human factor VIII, was sequenced. The predicted amino acid sequence is shown in Sequence ID No. 6.

Although only the A2 and B domains of porcine factor VIII have been sequenced entirely, the remainder of the porcine factor VIII molecule can be sequenced by standard cloning techniques, such as those described in Weis, J. H., "Construction of recombinant DNA libraries," in *Current Protocols in Molecular Biology*, F. M. Ausubel et al., eds. (1991), the teachings of which are incorporated herein by reference, so that full length hybrids can be constructed. Individual domains or parts of domains of porcine factor VIII cDNA can be cloned and substituted for the corresponding human domains or parts of domains by established mutagenesis techniques as described in Lubin, I. M., et al., "Elimination of a major inhibitor epitope in factor VIII," *J. Biol Chem.* (in press), the teachings of which are incorporated herein by reference. These factor VIII cDNA molecules can be cloned into expression vectors for ultimate expression of active hybrid human/porcine factor VIII protein molecules by established techniques, as described by Selden, R. F., "Introduction of DNA into mammalian cells," in *Current Protocols in Molecular Biology*, F. M. Ausubel et al., eds (1991), the teachings of which are incorporated herein by reference.

The same methods can be used to prepare other recombinant hybrid human/non-porcine mammalian factor VIII protein, such as hybrid human/mouse factor VIII.

DNA clones corresponding to the mouse homolog of the human factor VIII gene have been isolated and sequenced and the amino acid sequence of mouse factor VIII predicted, as described in Elder, G., et al., "Sequence of the Murine Factor VIII cDNA," 16(2) *Genomics* 374–379 (May 1993), the teachings of which are incorporated herein by reference, which also includes a comparison of the predicted amino acid sequences of mouse, human, and part of porcine factor VIII molecules. The mouse factor VIII cDNA sequence and predicted amino acid sequence are shown in Sequence ID No. 7 and Sequence ID No. 8, respectively.

Factor VIII sequences of other species for use in preparing a hybrid human/animal factor VIII molecule can be obtained using the RNA amplification with transcript sequencing (RAWTS) methods described in Sarkar, G., and S. S. Sommer, "Access to a Messenger RNA Sequence or Its Protein Product Is Not Limited by Tissue or Species Specificity," 244 *Science* 331–334 (1989), the teachings of which are incorporated herein by reference. Briefly, the steps are (1) cDNA synthesis with oligo (dT) or an mRNA-specific oligonucleotide primer; (2) polymerase chain reaction (PCR) in which one or both oligonucleotides contains a phage promoter attached to a sequence complementary to the region to be amplified; (3) transcription with a phage promoter; and (4) reverse transcriptase-mediated dideoxy sequencing of the transcript, which is primed with a nested (internal) oligonucleotide. In addition to revealing sequence information, this method can generate an in vitro translation product by incorporating a translation initiation signal into the appropriate PCR primer; and can be used to obtain novel mRNA sequence information from other species.

Substitution of amino acid(s):

According to Lollar, P., et al., 267 *J. Biol. Chem.* 23652–23657 (1992), the difference in coagulant activity between human and porcine factor VIII appears to be based on a difference in amino acid sequence between one or more residues in the A2 domain. Recombinant hybrid factor VIII molecules can be made by substitution of amino acid sequence from the porcine A2 domain into human factor VIII or amino acid sequence from the human A2 domain into porcine factor VIII, selecting in either case amino acid sequence that differs between the porcine and human molecules. These hybrid molecules can then be assayed by standard procedures for coagulant activity and for reactivity with inhibitory antibodies to human factor VIII for identification of hybrid factor VIII molecules with enhanced coagulant activity and/or decreased antibody reactivity. The methods used to prepare hybrid human/porcine factor VIII with substitution of amino acid sequence can be used to prepare recombinant hybrid human/mammalian factor VIII protein.

Both human and porcine A2 domains have 368 residues (Sequence ID Nos. 2 and 6, respectively). As shown in FIG. 2A–2B, which illustrates the alignment of the amino acid sequences of the human and porcine factor VIII A2 domains (residue numbering starts at position 373 with respect to the full length amino acid sequence of human factor VIII, Sequence ID No. 2), 50 of these residues are different and 318 are identical; i.e., there is an 86 percent sequence identity when human and porcine factor VIII A2 domains are aligned. Therefore, there is a large but finite number of combinations that would result in hybrid human/porcine factor VIII molecules with enhanced coagulant activity, based on these 50 differences.

Directed mutagenesis can be used to identify hybrid protein that has enhanced coagulant activity and/or decreased antibody reactivity. Specific human sequences can be replaced with animal sequences using oligonucleotide-directed mutagenesis, as was used to loop out the entire human A2 domain sequence (see example 7). A single residue or limited sequence in a human domain can be identified that, when changed to the corresponding animal sequence, results in a molecule with the procoagulant properties of the animal molecule or a molecule that does not react with inhibitory antibodies, as demonstrated in example 8.

For preparation of a hybrid human/porcine factor VIII molecule, the initial target candidates for mutagenesis, which were revealed upon comparison of the human and porcine A2 amino acid sequences (Sequence ID Nos. 2 and 6, respectively) within the human A2 domain, are shown in Table I.

TABLE 1

HUMAN AMINO ACID SEQUENCE TARGET CANDIDATES FOR MUTAGENESIS (Sequence ID No. 2)

| Sequence | Residues | Mismatches | Charge Changes |
| --- | --- | --- | --- |
| 398–403 | 6 | 4 | 1 |
| 434–444 | 10 | 4 | 3 |
| 484–496 | 13 | 7 | 3 |
| 598–603 | 6 | 4 | 2 |
| 536–541 | 6 | 4 | 0 |
| 713–722 | 10 | 6 | 2 |
| 727–737 | 11 | 6 | 2 |

Table I and the bold letters of FIG. 2A–2B illustrate seven sequences in the human and pig A2 domain amino acid sequences (Sequence ID Nos. 2 and 6, respectively) that constitute only 17 percent of the A2 domain but include 70 percent of the sequence differences between human and porcine A2 domains. Initially, all seven hybrids can be made by substituting the porcine sequence into the human A2 domain. As functional analysis of each of these hybrids reveals coagulant activity with or without decreased reactivity with inhibitory antibodies, the sequence can be further dissected by point mutation analysis, using standard site-directed mutagenesis techniques.

This approach can be used to identify one or more critical region(s) that underlie the superior coagulant activity of porcine factor VIII, allowing production of effective procoagulant hybrid factor VIII. It can also be used to identify regions in the A2 or other domains to which antibodies are directed. Over 90 percent of inhibitory antibodies to human factor VIII are directed against either the A2 or C2 domains or both. The latter domain consists of amino acid residues 2183–2332 (Sequence ID No. 2). Within this 154 amino acid region, inhibitor activity appears to be directed to a 65 amino acid region between residues 2248 and 2312, according to Shima, M., et al., 69 *Thromb. Haemostas.* 240–246 (1993). Hybrid human/animal factor VIII molecules having decreased or no reactivity with inhibitor antibodies can be prepared by cloning and expressing animal factor VIII C2 or A2 cDNA and substituting porcine or other non-human mammalian C2 and/or A2 sequence for human C2 and/or A2 sequence. If the C2 sequence of human and porcine factor VIII is approximately 85 percent identical in this region, as it is elsewhere in the functionally active regions of factor VIII, there will be approximately ten differences between human and porcine factor VIII C2 amino acid sequence, which can be used as initial targets to construct hybrids with substituted C2 sequence.

Similar analyses and comparisons can be made between the sequence of human and other animal factor VIII molecules, and similar methods can be used to prepare other hybrid human/animal factor VIII molecules. As described above, functional analysis of each hybrid will reveal those with decreased reactivity to inhibitory antibodies and or increased coagulant activity, and the sequence can be further dissected by point mutation analysis For example, hybrid human/mouse factor VIII molecules can be prepared as described above. The amino acid sequence alignment of the A2 domain of human (Sequence ID No. 2) and mouse (Sequence ID No. 8) is shown in FIG. 2A–2B. As reported by Elder et al., the factor VIII protein encoded by the mouse cDNA (Sequence ID No. 7) has 2319 amino acids, with 74% sequence identity overall to the human sequence (Sequence ID No. 2) (87 percent identity when the B domain is excluded from the comparison), and is 32 amino acids shorter than human factor VIII. The amino acid sequences in the mouse A and C domains (Sequence ID No. 8) are highly conserved, with 84–93 percent sequence identity to the human sequence (Sequence ID No. 2), while the other domains have 42–70 percent sequence identity. Specifically, the A1, A2, and A3 mouse amino acid sequences (Sequence ID No. 8) are 85, 85, and 90 percent identical to the corresponding human amino acid sequences (Sequence ID No. 2). The C1 and C2 mouse amino acid sequences are 93 and 84 percent identical to the corresponding human amino acid sequences. In the predicted mouse factor VIII amino acid sequence (Sequence ID No. 8), the A1, A2, and A3 domains include amino acids 1–330, 380–711, and 1664–1987, respectively, using amino acid sequence homology for numbering purposes.

The thrombin/factor Xa and all but one activated protein C cleavage sites are conserved in mouse factor VIII. The tyrosine residue for von Willebrand factor binding is also conserved.

According to Elder et al., the nucleotide sequence (Sequence ID No. 7) of mouse factor VIII contains 7519 bases and has 67 percent identity overall with the human nucleotide sequence (Sequence ID No. 1). The 6957 base pairs of murine coding sequence have 82 percent sequence identity with the 7053 base pairs of coding sequence in human factor VIII. When the B domain is not included in the comparison, there is an 88 percent nucleotide sequence identity.

Elder et al. report that although human and mouse factor VIII molecules are only 74 percent identical overall, 95 percent of the human residues that lead to hemophilia when altered are identical in the mouse.

Preparation of hybrid human/animal factor VIII equivalents:

The methods described above and in the examples can also be used to prepare active hybrid human/animal factor VIII equivalent molecules. A sequence of one or more amino acid residues in human or animal factor VIII or hybrid human/animal factor VIII that functions as an antigenic site which is immunoreactive with endogenous factor VIII inhibitory antibodies can be identified as described, and then can be substituted with a sequence of one or more amino acid residues having no known homology to human or animal factor VIII sequence which does not form an antigenic site immunoreactive with endogenous factor VIII inhibitory antibodies. One or more antigenic sites can be substituted to form an active hybrid factor VIII equivalent molecule. The resulting active hybrid human/animal factor VIII equivalent molecule has less reactivity with factor VIII inhibitory antibodies than the unsubstituted human or animal or hybrid human/animal factor VIII.

Alternatively or additionally, active hybrid human/animal factor VIII equivalent molecules can be prepared, using the methods described above and in the examples, in which a sequence of one or more amino acid residues in human or animal factor VIII or hybrid human/animal factor VIII that is critical to the coagulant activity, can be identified as described, and then can be substituted with a sequence of one or more amino acid residues having no known homology to human or animal factor VIII sequence which also provides coagulant activity. One or more coagulant activity sequences can be substituted to form an active hybrid factor VIII equivalent molecule. The resulting active hybrid human/animal factor VIII equivalent molecule has coagulant activity that may be less than, equal to, or greater than that of the unsubstituted factor VIII molecule. Preferably, the hybrid factor VIII equivalent molecule has coagulant activity that is superior to that of human factor VIII.

Suitable sequences of one or more amino acid residues that can be substituted for those sequences of amino acids critical to coagulant and/or antigenic activity in human or animal factor VIII or hybrid human/animal factor VIII include any sequence of one or more amino acids not homologous to animal or human factor VIII amino acid sequence that has coagulant activity and/or has less reactivity with endogenous inhibitory antibodies to factor VIII.

Hybrid human/animal factor VIII equivalent molecules can have substitutions of one or more amino acid sequences for coagulant activity and/or one or more amino acid sequences for antigenic sites. Hybrid human/animal factor VIII equivalent molecules described herein also include those molecules in which amino acid residues not critical to coagulant activity or antigenic activity are substituted with amino acid residues having no known homology to animal factor VIII sequence.

Diagnostic Assays

The hybrid human/animal cDNA and/or protein expressed therefrom, in whole or in part, can be used in assays as diagnostic reagents for the detection of inhibitory antibodies to human or animal factor VIII or to hybrid human/animal factor VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the hybrid human/animal factor VIII that contains at least one antigenic site, wherein the amount is sufficient to form a detectable complex with the inhibitory antibodies in the sample.

Nucleic acid and amino acid probes can be prepared based on the sequence of the hybrid human/animal factor VIII molecule. These can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a hybrid human/animal factor VIII.

Pharmaceutical Compositions

Pharmaceutical compositions containing hybrid human/animal factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin, the teachings of which are incorporated herein by reference.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid human/animal factor VIII is then introduced into the container. The container is then swirled by hand to free lipid material from the sides of the container and to disperse lipid aggregates, thereby forming the liposomal suspension.

The hybrid human/animal factor VIII can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Hybrid human/animal factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, 29 Transfusion 812–820, 1989).

Hybrid human/animal factor VIII can be stored bound to vWf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of hybrid human/animal factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid human/animal factor VIII has been indefinitely stable at 4° C. in 0.6M NaCl, 20 mM MES, and 5 mM $CaCl_2$ at pH 6.0 and also can be stored frozen in these buffers and thawed with minimal loss of activity.

Methods of Treatment

Hybrid human/animal factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, hybrid human/animal factor VIII can be administered by transplant of cells genetically engineered to produce the hybrid or by implantation of a device containing such cells, as described above.

In a preferred embodiment, pharmaceutical compositions of hybrid human/animal factor VIII alone or in combination with stabilizers, delivery vehicles, and/or carriers are infused into patients intravenously according to the same procedure that is used for infusion of human or animal factor VIII.

The treatment dosages of hybrid human/animal factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid human/animal factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M., et al., 328 New. Engl. J. Med. 453–459 (1993); Pittman, D. D., et al., 79 Blood 389–397 (1992), and Brinkhous et al., 82 Proc. Natl. Acad. Sci. 8752–8755 (1985).

Usually, the desired plasma factor VIII level to be achieved in the patient through administration of the hybrid human/animal factor VIII is in the range of 30–100% of normal. In a preferred mode of administration of the hybrid human/animal factor VIII, the composition is given intravenously at a preferred dosage in the range from about 20 to 50 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in Hematology, Williams, W. J., et al., ed. (1990). Patients with inhibitors may require more hybrid human/animal factor VIII, or patients may require less hybrid human/animal factor VIII because of its higher specific activity than human factor VIII or decreased antibody reactivity. As in treatment with human or porcine factor VIII, the amount of factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, hybrid human/animal factor VIII can be administered subcutaneously or orally with liposomes in one or several doses at varying intervals of time.

Hybrid human/animal factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

The hybrid human/animal factor VIII molecule and the methods for isolation, characterization, making, and using it generally described above will be further understood with reference to the following non-limiting examples.

EXAMPLE 1

Assay of porcine factor VIII and hybrid human/porcine factor VIII

Porcine factor VIII has more coagulant activity than human factor VIII, based on specific activity of the molecule. These results are shown in Table III in Example 4. This conclusion is based on the use of appropriate standard curves that allow human and porcine factor VIII to be fairly compared. Coagulation assays are based on the ability of factor VIII to shorten the clotting time of plasma derived from a patient with hemophilia A. Two types of assays were employed: the one-stage and the two-stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15M NaCl, 0.02M HEPES, pH 7.4. The standard curve was constructed based on 3 or 4 dilutions of plasma, the highest dilution being 1/50, and on $log_{10}$ clotting time plotted against $log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2

Characterization of the functional difference between human and porcine factor VIII The isolation of porcine and human plasma-derived factor VIII and human recombinant factor VIII have been described in the literature in Fulcher, C. A., and T. S. Zimmerman, 79 *Proc. Nat'l. Acad. Sci. U.S.A.* 1648–1652 (1982); Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); Fass, D. N., et al., 59 *Blood* 594 (1982); Toole, J. J., et al., 83 *Proc. Nat'l. Acad. Sci. U.S.A.* 5939–5942 (1986), the teachings of all of which are incorporated herein by reference. This can be accomplished in several ways. All these preparations are similar in subunit composition, although this is the first description of the functional difference between human and porcine factor VIII, not noted previously in part due to the lack of use of a common standard by which to compare them.

For comparison of human recombinant and porcine factor VIII, preparations of highly-purified human recombinant factor VIII (Cutter Laboratories, Berkeley, Calif.) and porcine factor VIII (immunopurified as described in Fass, D. N., et al., 59 *Blood* 594 (1982)) were subjected to high-pressure liquid chromatography (HPLC) over a Mono Q™ (Pharmacia-LKB, Piscataway, N.J.) anion-exchange column (Pharmacia, Inc.). The purposes of the Mono Q™ HPLC step were elimination of minor impurities and exchange of human and porcine factor VIII into a common buffer for comparative purposes. Vials containing 1000–2000 units of factor VIII were reconstituted with 5 ml $H_2O$. Hepes (2M at pH 7.4) was then added to a final concentration of 0.02M. Factor VIII was applied to a Mono Q™ HR 5/5 column equilibrated in 0.15M NaCl, 0.02M Hepes, 5 mM $CaCl_2$, at pH 7.4 (Buffer A plus 0.15M NaCl); washed with 10 ml Buffer A+0.15M NaCl ;and eluted with a 20 ml linear gradient, 0.15M to 0.90M NaCl in Buffer A at a flow rate of 1 ml/min.

For comparison of human factor VIII (derived from plasma and purified by Mono Q™ HPLC) and porcine factor VIII, immunoaffinity-purified, plasma-derived porcine factor VIII was diluted 1:4 with 0.04M Hepes, 5 mM $CaCl_2$, 0.01% Tween-80, at pH 7.4, and subjected to Mono Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE FACTOR VIII COAGULANT ACTIVITY

| | Activity (U/$A_{280}$) |
| --- | --- |
| Porcine | 21,300 |
| Human plasma-derived | 3,600 |
| Human recombinant | 2,400 |

EXAMPLE 3

Comparison of the stability of human and porcine factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono Q™ HPLC-purified human factor VIII was activated with thrombin and subjected to Mono S™ cation-exchange (Pharmacia, Inc.) HPLC under conditions that produce stable porcine factor VIIIa, as described by Lollar, J. S., and C. G. Parker, 28 *Biochemistry* 666 (1989), the teachings of which are incorporated herein by reference.

Human factor VIII, 43 μg/ml (0.2 μM) in 0.2M NaCl, 0.01M Hepes, 2.5 mM $CaCl_2$, at pH 7.4, in 10 ml total volume, was reacted with thrombin (0.036 μM) for 10 min, at which time FPR-CH$_2$Cl D-phenyl-prolyl-arginyl-chloromethyl ketone was added to a concentration of 0.2 μM for irreversible inactivation of thrombin. The mixture then was diluted 1:1 with 40 mM 2-(N-morpholino)ethane sulfonic acid (MES), 5 mM CaCl$_2$, at pH 6.0, and loaded at 2 ml/min onto a Mono S™ HR 5/5 HPLC column (Pharmacia, Inc.) equilibrated in 5 mM MES, 5 mM CaCl$_2$, at pH 6.0 (Buffer B) plus 0.1M NaCl. Factor VIIIa was eluted without column washing with a 20 ml gradient from 0.1M NaCl to 0.9M NaCl in Buffer B at 1 ml/min.

The fraction with coagulant activity in the two-stage assay eluted as a single peak under these conditions. The specific activity of the peak fraction was approximately 7,500 U/A$_{280}$. Sodium dodecyl sulfate-polyacrylamide gel electrophoresis (SDS-PAGE) of the Mono S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by Mono S™ HPLC under the same conditions had a specific activity 1.6×10$^6$ U/A$_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of Mono S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimeric factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S™ buffers to pH 5. Mono Q™-purified human factor VIII (0.5 mg) was diluted with H$_2$O to give a final composition of 0.25 mg/ml (1 μM) factor VIII in 0.25M NaCl, 0.01M Hepes, 2.5 mM CaCl$_2$, 0.005% Tween-80, at pH 7.4 (total volume 7.0 ml). Thrombin was added to a final concentration of 0.072 μM and allowed to react for 3 min. Thrombin was then inactivated with FPR-CH$_2$Cl (0.2 μM). The mixture then was diluted 1:1 with 40 mM sodium acetate, 5 mM CaCl$_2$, 0.01% Tween-80, at pH 5.0, and loaded at 2 ml/min onto a Mono S™ HR 5/5 HPLC column equilibrated in 0.01M sodium acetate, 5 mM CaCl$_2$, 0.01% Tween-80, at pH 5.0, plus 0.1M NaCl. Factor VIIIa was eluted without column washing with a 20 ml gradient from 0.1M NaCl to 1.0M NaCl in the same buffer at 1 ml/min. This resulted in recovery of coagulant activity in a peak that contained detectable amounts of the A2 fragment as shown by SDS-PAGE and silver staining. The specific activity of the peak fraction was ten-fold greater than that recovered at pH 6.0 (75,000 U/A$_{280}$ vs. 7,500 U/A$_{280}$). However, in contrast to porcine factor VIIIa isolated at pH 6.0, which is indefinitely stable at 4° C., human factor VIIIa activity decreased steadily over a period of several hours after elution from Mono S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4

Preparation of hybrid human/porcine factor VIII by reconstitution with subunits

Porcine factor VIII light chains and factor VIII heavy chains were isolated as follows. A 0.5M solution of EDTA at pH 7.4 was added to Mono Q™-purified porcine factor VIII to a final concentration of 0.05M and was allowed to stand at room temperature for 18–24 h. An equal volume of 10 mM histidine-Cl, 10 mM EDTA, 0.02% v/v Tween 80, at pH 6.0 (Buffer B), was added, and the solution was applied at 1 ml/min to a Mono S™ HR 5/5 column previously equilibrated in Buffer A plus 0.25M NaCl. Factor VIII heavy chains did not bind the resin, as judged by SDS-PAGE. Factor VIII light chain was eluted with a linear, 20 ml, 0.1–0.7M NaCl gradient in Buffer A at 1 ml/min and was homogeneous by SDS-PAGE. Factor VIII heavy chains were isolated by mono Q™ HPLC (Pharmacia, Inc., Piscataway, N.J.) in the following way. Factor VIII heavy chains do not adsorb to mono S™ during the purification of factor VIII light chains. The fall-through material that contained factor VIII heavy chains was adjusted to pH 7.2 by addition of 0.5M Hepes buffer, pH 7.4, and applied to a mono Q™ HR5/5 HPLC column (Pharmacia, Inc.) equilibrated in 0.1M NaCl, 0.02M Hepes, 0.01% Tween-80, pH 7.4. The column was washed with 10 ml of this buffer, and factor VIII heavy chains were eluted with a 20 ml 0.1–1.0M NaCl gradient in this buffer. Human light chains and heavy chains were isolated in the same manner.

Human and porcine light and heavy chains were reconstituted according to the following steps. Ten μl human or porcine factor VIII light chain, 100 μg/ml, was mixed in 1M NaCl, 0.02M Hepes, 5 mM CaCl$_2$, 0.01% Tween-80, pH 7.4, with (1) 25 μl heterologous heavy chain, 60 μg/ml, in the same buffer; (2) 10 μl 10.02M Hepes, 0.01% Tween-80, pH 7.4; (3) 5 μl 10.6M CaCl$_2$, for 14 hr at room temperature. The mixture was diluted 1/4 with 0.02M MES, 0.01% Tween-80, 5 mM CaCl$_2$, pH 6, and applied to Mono S™ Hr5/5 equilibrated in 0.1M NaCl, 0.02M MES, 0.01% Tween-80, 5 mM CaCl$_2$, pH 6.0. A 20 ml gradient was run from 0.1–1.0M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds Mono S™; excess heavy chains ensure that free light chains are not part of the preparation. Reconstitution experiments followed by Mono S™ HPLC purification were performed with all four possible combinations of chains: human light chain/human heavy chain, human light chain/porcine heavy chain, porcine light chain/porcine heavy chain, porcine light chain/human heavy chain.

Table III shows that human light chain/porcine heavy chain factor VIII has activity comparable to native porcine factor VIII (Table II), indicating that structural elements in the porcine heavy chain are responsible for the increased coagulant activity of porcine factor VIII compared to human factor VIII.

TABLE III

COMPARISON OF HYBRID HUMAN/PORCINE FACTOR VIII COAGULANT ACTIVITY WITH HUMAN AND PORCINE FACTOR VIII

| | Activity (U/A$_{280}$) |
|---|---|
| Porcine light chain/porcine heavy chain | 30,600 |
| Human light chain/porcine heavy chain | 44,100 |
| Porcine light chain/human heavy chain | 1,100 |
| Human light chain/human heavy chain | 1,000 |

EXAMPLE 5

Preparation of active hybrid human/porcine factor VIII by reconstitution with domains The porcine A1/A3-C1-C2 dimer, the porcine A2 domain, the human A1/A3-C1-C2 dimer, and the human A2 domain were each isolated from porcine or human blood, according to the method described in Lollar, P., et al., 267(33) *J. Biol. Chem.* 23652–23657 (Nov. 25, 1992). For example, to isolate the porcine A1A3-C1-C2 dimer, porcine factor VIIIa (140 μg) at pH 6.0 was raised to pH 8.0 by addition of 5N NaOH for 30 minutes, producing dissociation of the A2 domain and 95 percent inactivation by clotting assay. The mixture was diluted 1:8 with buffer B (20 mM HEPES, 5 mM CaCl$_2$, 0.01% Tween 80, pH 7.4) and applied to a monoS column equilibrated in buffer B. The A1/A3-C1-C2 dimer eluted as a single sharp peak at approximately 0.4M NaCl by using a 0.1–1.0M NaCl gradient in buffer B. To isolate the porcine A2 domain, porcine factor VIIIa was made according to the method of Lollar, P., and C. G. Parker, 28 *Biochem.* 666–674 (1989), starting with 0.64 mg of factor VIII. Free porcine A2 domain was isolated as a minor component (50 μg) at 0.3M NaCl in the monoS™ chromatogram.

Hybrid human/porcine factor VIII molecules were reconstituted from the dimers and domains as follows. The concentrations and buffer conditions for the purified components were as follows: porcine A2, 0.63 μM in buffer A (5 mM MES; 5 mM CaCl$_2$, 0.01% Tween 80, pH 6.0) plus 0.3M NaCl; porcine A1/A3-C1-C2, 0.27 μM in buffer B plus 0.4M NaCl, pH 7.4; human A2, 1 μM in 0.3M NaCl, 10 mM histidine-HCl, 5 mM CaCl$_2$, 0.01% Tween 20, pH 6.0; human A1/A3-C1-C2, 0.18 μM in 0.5M NaCl, 10 mM histidine-Cl, 2.5 mM CaCl$_2$, 0.1% Tween 20, pH 6.0. Reconstitution experiments were done by mixing equal volumes of A2 domain and A1/A3-C1-C2 dimer. In mixing experiments with porcine A1/A3-C1-C2 dimer, the pH was lowered to 6.0 by addition of 0.5M MES, pH 6.0, to 70 mM.

The coagulation activities of all four possible hybrid factor VIIIa molecules-[pA2/(hA1/A3-C1-C2)], [hA2/(pA1/A3-C1-C2)], [pA2/(pA1/pA3-C1-C2)], and [hA2/(hA1/A3-C1-C2)]-were obtained by a two-stage clotting assay at various times.

The generation of activity following mixing the A2 domains and A1/A3-C1-C2 dimers was nearly complete by one hour and was stable for at least 24 hours at 37° C. Table IV shows the activity of reconstituted hybrid factor VIIIa molecules when assayed at 1 hour. The two-stage assay, by which the specific activities of factor VIIIa molecules were obtained, differs from the one-stage assay, and the values cannot be compared to activity values of factor VIII molecules obtained by a one-stage assay.

TABLE IV

COMPARISON OF COAGULANT ACTIVITIES OF DOMAIN-SUBSTITUTED HYBRID HUMAN/PORCINE FACTOR VIII

| Hybrid fVIIIa | Specific Activity (U/mg) |
|---|---|
| Porcine A2 + Human A1/A3-C1-C2 | 140,000 |
| Porcine A2 + Porcine A1/A3-C1-C2 | 70,000 |
| Human A2 + Porcine A1/A3-C1-C2 | 40,000 |
| Human A2 + Human A1/A3-C1-C2 | 40,000 |

Table IV shows that the greatest activity was exhibited by the porcine A2 domain/human A1/A3-C1-C2 dimer, followed by the porcine A2 domain/porcine A1/A3-C1-C2 dimer.

Thus, when the A2 domain of porcine factor VIIIa was mixed with the A1/A3-C1-C2 dimer of human factor VIIIa, coagulant activity was obtained. Further, when the A2 domain of human factor VIIIa was mixed with the A1/A3-C1-C2 dimer of porcine factor VIIIa, coagulant activity was obtained. By themselves, the A2, A1, and A3-C1-C2 regions have no coagulant activity.

EXAMPLE 6

Isolation and sequencing of the A2 domain of porcine factor VIII

Only the nucleotide sequence (Sequence ID No. 4) encoding the B domain and part of the A2 domain of porcine factor VIII has been sequenced previously (Toole, J. J., et al., 83 *Proc. Nat'l. Acad. Sci. U.S.A.* 5939–5942 (1986)). The cDNA and predicted amino acid sequences (Sequence ID Nos. 5 and 6, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript™ (Stratagene) phagemid vector.

The porcine A2 domain was completely sequenced by dideoxy sequencing. The cDNA and predicted amino acid sequences are as described in Sequence ID Nos. 5 and 6, respectively.

EXAMPLE 7

Preparation of recombinant hybrid human/animal factor VIII

The nucleotide and predicted amino acid sequences (Sequence ID Nos. 1 and 2, respectively) of human factor VIII have been described in the literature (Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech)).

Making recombinant hybrid human/animal factor VIII requires that a region of human factor VIII cDNA (Biogen Corp.) be removed and the homologous animal cDNA sequence be inserted. Subsequently, the hybrid cDNA is expressed in an appropriate expression system. As an example, three hybrid factor VIII cDNAs were cloned in which some or all of the porcine A2 domain was substituted for the corresponding human A2 sequences. Initially, the entire cDNA sequence corresponding to the A2 domain of human factor VIII was removed by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989).

The steps were as follows: *E. coli* CJ236 cells were transformed with Bluescript™ phage containing the human factor VIII cDNA insert. Single-stranded Bluescript™/human factor VIII circular DNA was produced with M13K07 helper phage and then purified by standard methods (Sambrook, J., E. F. Fritsch, and T. Maniatis, *Molecular Cloning: A Laboratory Manual*, Chapter 4, Cold Spring Harbor Press, Cold Spring Harbor, 1989). A mutagenic oligonucleotide (SEQ ID NO: 9) was synthesized corresponding to the 3' end of the A1 domain and the 5' end Of the A3 domain:

5' CCTTCCTTTATCCAAATACGTAGATCAA-GAGGAAATTGAC 3'.

Additionally this oligonucleotide provides a SnaB1 restriction site that can be used to insert the porcine A2 domain. On hybridization of this oligonucleotide to single strand Bluescript™/human factor VIII, the region between the A1 and A3 domains, i.e., the A2 domain, was "looped out." The resulting heteroduplex was extended to circular, double-stranded DNA by use of T7 polymerase, ligated, and used to transform *E. coli* XL1-blue™ (Stratagene) cells. Transformants were screened by isolation of phagemid DNA from several colonies, Xho1 digestion, and examination of the size of phagemid DNA by agarose gel electrophoresis. Three clones were identified that were shorter than human factor VIII/Bluescript™ by 1 kb, as expected for deletion of the 1 kb A2 domain. The results were confirmed by sequencing across the boundaries of the A1 and A3 domains.

The porcine A2 domain was inserted between the A1 and A3 domains of the human factor VIII cDNA by (1) PCR amplification of the porcine A2 domain; (2) gel purification of the PCR product (agarose gel electrophoresis of the PCR product producing a band visualized by ethidium bromide staining, followed by excision of the band and purification of the DNA to remove agarose and other contaminants); and (3) ligation by using T4 DNA ligase of the porcine A2 cDNA to the human A2-domainless cDNA linearized by using the SnaB1 restriction site. The primers used for PCR amplification of the porcine A2 are shown in the Sequence Listing as SEQ ID NOs:10 and 11.

The 3' primer contains nucleotides corresponding to residues 736–740 of the porcine factor VIII protein sequence (Sequence ID No. 6) (at the C-terminus of the A2 domain), and residues 1649–1656 of the human factor VIII sequence (Sequence ID No. 2) (at the N-terminus of the A3 domain). The A3 sequence residues were included because the looping out procedure removed these residues. The ligated product was used to transform XL1-Blue cells, producing several colonies that contained the desired porcine A2 insert when analyzed by PCR. The product contains an unwanted thymine at the A1–A2 junction as a result of the PCR amplification of the porcine A2 domain. This single base can be looped out by use of the mutagenic oligonucleotide Shown in Sequence listing as SEQ ID NO:12, and the product can be cloned exactly as described above (under Example 6, paragraph 3) for the production of human A2-deficient nucleotide. This product, in which a complete A2 substitution was obtained, was designated H/P fVIII-1.

H/P fVIII-1 was inserted into several expression vectors, but attempts to express active hybrid factor VIII in COS-7 cells and baby hamster kidney cells have yielded no activity and no detectable fVIII protein by immunoassay.

Figure 3:
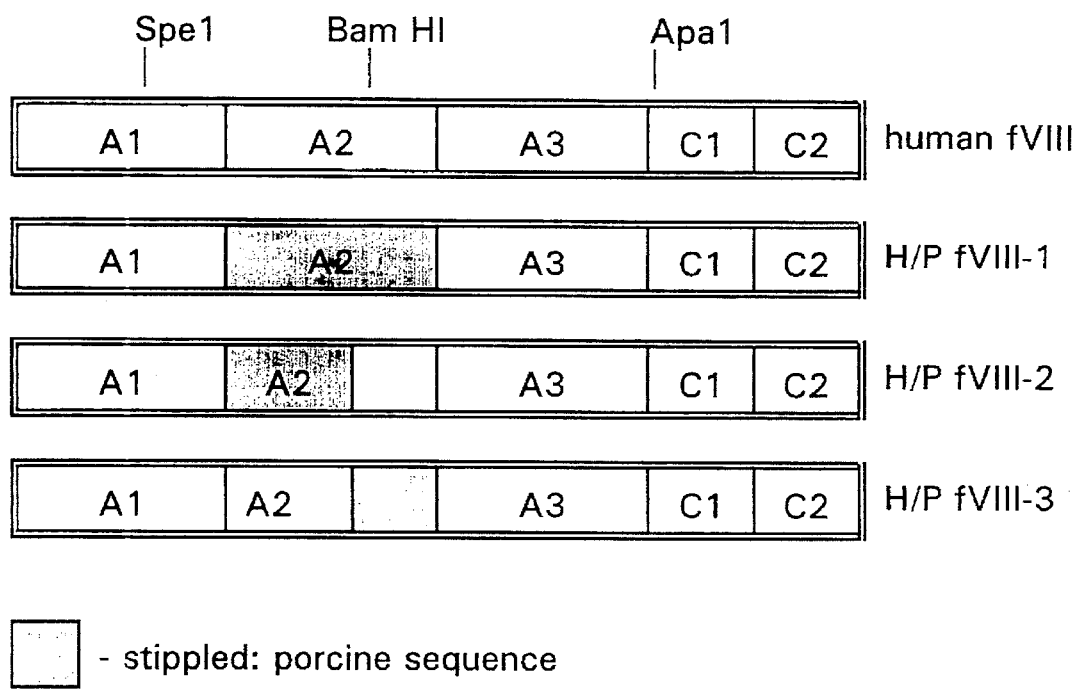
FIG. 3 is a diagrammatic representation of hybrid human/porcine factor VIII molecules in which all or part of the porcine A2 domain is substituted for the homologous human A2 domain or partial domain in human factor VIII by recombinant technology.

Two additional hybrids, designated H/P fVIII-2 and H/P fVIII-3, were prepared as follows. A unique Bam HI restriction site at position 1869 within the A2 domain of the human and porcine sequences, as well as a unique SpeI site at position 585 in the A1 domain of human fVIII were used to produce two additional hybrid molecules. SpeI-Bam HI fragments were cut out of human B-domainless factor VIII and H/P fVIII-1 in pBluescript and purified along with the corresponding fragment consisting of pBluescript and the factor VIII insert minus the SpeI-Bam HI fragment. Then the H/P fVIII-1 SpeI-Bam HI fragment was ligated into the human factor VIII Bluescript fragment lacking the SpeI-Bam HI fragment, and the human factor VIII SpeI-Bam HI fragment was ligated into the H/P fVIII-1 Bluescript fragment lacking the SpeI-Bam HI fragment, producing H/P fVIII-2, in which the NH$_2$-terminal 63 percent of the human A2 domain is replaced by the corresponding porcine A2 domain, and H/P fVIII-3, in which the COOH-terminal 37 percent of the human A2 domain is replaced by the corresponding porcine A2 domain. These human/porcine factor VIII hybrids are illustrated in FIG. 3.

Next, two unique restriction sites, SpeI and ApaI, which are in the A1 and C1 domains, respectively, were used to put H/P fVIII-1, H/P fVIII-2, and H/P fVIII-3 into the expression vector ReNeo. The SpeI-ApaI fragments of human B-domainless factor VIII, H/P fVIII-1, H/P fVIII-2, and H/P fVIII-3, all in pBluescript, were cut out and purified. Activity was obtained from the H/P fVIII-2 construct (2,700±200 units/mg) that was essentially identical to that of the wild type construct (2,600±200 units/mg).

Cloning of other animal A1, A3, C1, and C2 domains is feasible with the same strategy that was used for cloning the porcine A2 domain. Fragments of these domains can be cloned by the looping out mutagenesis technique. Excision of the corresponding domains in human factor VIII and any fragments thereof, including single amino acid eliminations, is feasible by looping out mutagenesis as described above. All possible domain replacements, fragments of domain replacements, or single amino acid residue replacements are possible by this approach.

The biological activity of recombinant hybrid human/animal factor VIII with A1, A3, C1, and/or C2 domain substitutions can be evaluated initially by use of a COS-cell mammalian transient expression system. Hybrid human/animal cDNA can be transfected into COS cells, and supernatants can be analyzed for factor VIII activity by use of one-stage and two-stage coagulation assays as described above in Example 1. Additionally, factor VIII activity can be measured by use of a chromogenic substrate assay, which is more sensitive and allows analysis of larger numbers of samples. This assay has been described (Lollar, P., G. J. Knutson, and D. N. Fass, 24 *Biochemistry* 8056–8064, 1985). Similar assays are standard in the assay of factor VIII activity (Wood, W. I., et al., 312 *Nature* 330–337, 1984; Toole, J. J., et al., 312 *Nature* 342–347, 1984). Expression of recombinant factor VIII in COS cells is also a standard procedure (Toole, J. J., et al., 312 *Nature* 342–1347, 1984; Pittman, D. D., and R. J. Kaufman, 85 *Proc. Nat'l. Acad. Sci. U.S.A.* 2429–2433, 1988). The human factor VIII cDNA used as starting material for the recombinant molecules described herein has been expressed in COS cells yielding a product with biological activity. This material can be used as a standard to compare hybrid human/animal factor VIII molecules. The activity in the assays is converted to a specific activity for proper comparison of the hybrid molecules. For this, a measurement of the mass of factor VIII produced by the cells is necessary and can be done by immunoassay with purified human and/or animal factor VIII as standards. Immunoassays for factor VIII are routine for those skilled in the art (See, e.g., Lollar, P., et al., 71 *Blood* 137–143, 1988).

EXAMPLE 8

Determination of inhibitory activity in hybrid human/animal factor VIII

Sequences of human and animal factor VIII likely to be involved as epitopes (i.e., as recognition sites for inhibitory antibodies) can be determined through use of commercially available predictive computer programs, such as MacVector (IBI Corp., New Haven, Conn.) or by assay with antibodies to factor VIII, as shown in the following experiment. Sequences of animal factor VIII that are not antigenic compared to corresponding (homologous) antigenic human sequences will be identified, and substitutions will be made to insert animal sequences and delete human sequences according to standard recombinant DNA methods. It is already known that porcine factor VIII reacts less than human factor VIII with some inhibitory antibodies; this provides a basis for current therapy for patients with inhibitors. After the recombinant hybrids are made, they will be tested in vitro for reactivity with the Bethesda inhibitor assay. Those constructs that are less reactive than native human factor VIII and native animal factor VIII will be candidates for replacement therapy.

Expression of hybrid human/porcine factor VIII (H/P fVIII-2) (see Example 7) activity has been measured in the presence and absence of an inhibitory monoclonal antibody, 413 (mAb413) (obtained from Dr. Dorothea Scandella, American Red Cross, Rockville, Md.), that binds to a region of the human factor VIII that is the same as or is closely adjacent to a region recognized by human anti-A2 inhibitory antibodies, but does not react with porcine factor VIII. The epitope recognized by human anti-A2 antibodies was localized to the $NH_2$-terminal half of the human A2 domain (residue 373–536, Sequence ID No. 2) by immunoblotting and deletion mapping. There was no detectable inhibition of H/P fVIII-2 activity by up to 40 nM mAb413, whereas the wild type construct was inhibited by 50 percent by 1.0 nM mAb413. Thus, an active hybrid human/porcine factor VIII molecule, H/P fVIII-2, has been expressed that lacks the epitope recognized by anti-A2 domain autoantibodies and alloantibodies.

Although only preferred embodiments are specifically illustrated and described herein, it will be appreciated that many modifications and variations of the present invention are possible in light of the above teachings and within the purview of the appended claims without departing from the spirit and intended scope of the invention.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 9009 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapien
        ( F ) TISSUE TYPE: Liver ( i x ) FEATURE:
        ( A ) NAME/KEY: misc_feature (Domain Structure)
        ( B ) LOCATION: 5125 . . . 7053
        ( D ) OTHER INFORMATION: /note= "Equivalent to the A3-C1-C2 domain"

( i x ) FEATURE:
        ( A ) NAME/KEY: misc_feature (Domain Structure)
        ( B ) LOCATION: 1 . . . 2277
        ( D ) OTHER INFORMATION: /note= "Equivalent to the A1-A2 domain."

( i x ) FEATURE:
        ( A ) NAME/KEY: Domain
        ( B ) LOCATION: 1..2277
        ( D ) OTHER INFORMATION: /note= "cDNA encoding human factor

VIII."

( x i ) SEQUENCE DESCRIPTION: SEQ ID NO:1:

| | | | | | | |
|---|---|---|---|---|---|---|
| CAGTGGGTAA | GTTCCTTAAA | TGCTCTGCAA | AGAAATTGGG | ACTTTTCATT | AAATCAGAAA | 60 |
| TTTTACTTTT | TTCCCCTCCT | GGGAGCTAAA | GATATTTTAG | AGAAGAATTA | ACCTTTTGCT | 120 |
| TCTCCAGTTG | AACATTTGTA | GCAATAAGTC | ATGCAAATAG | AGCTCTCCAC | CTGCTTCTTT | 180 |
| CTGTGCCTTT | TGCGATTCTG | CTTTAGTGCC | ACCAGAAGAT | ACTACCTGGG | TGCAGTGGAA | 240 |
| CTGTCATGGG | ACTATATGCA | AAGTGATCTC | GGTGAGCTGC | CTGTGGACGC | AAGATTTCCT | 300 |
| CCTAGAGTGC | CAAAATCTTT | TCCATTCAAC | ACCTCAGTCG | TGTACAAAAA | GACTCTGTTT | 360 |
| GTAGAATTCA | CGGTTCACCT | TTTCAACATC | GCTAAGCCAA | GGCCACCCTG | GATGGGTCTG | 420 |
| CTAGGTCCTA | CCATCCAGGC | TGAGGTTTAT | GATACAGTGG | TCATTACACT | TAAGAACATG | 480 |
| GCTTCCCATC | CTGTCAGTCT | TCATGCTGTT | GGTGTATCCT | ACTGGAAAGC | TTCTGAGGGA | 540 |
| GCTGAATATG | ATGATCAGAC | CAGTCAAAGG | GAGAAGAAG | ATGATAAAGT | CTTCCCTGGT | 600 |
| GGAAGCCATA | CATATGTCTG | GCAGGTCCTG | AAAGAGAATG | GTCCAATGGC | CTCTGACCCA | 660 |
| CTGTGCCTTA | CCTACTCATA | TCTTTCTCAT | GTGGACCTGG | TAAAAGACTT | GAATTCAGGC | 720 |
| CTCATTGGAG | CCCTACTAGT | ATGTAGAGAA | GGGAGTCTGG | CCAAGGAAAA | GACACAGACC | 780 |
| TTGCACAAAT | TTATACTACT | TTTTGCTGTA | TTTGATGAAG | GGAAAAGTTG | GCACTCAGAA | 840 |
| ACAAAGAACT | CCTTGATGCA | GGATAGGGAT | GCTGCATCTG | CTCGGGCCTG | GCCTAAAATG | 900 |
| CACACAGTCA | ATGGTTATGT | AAACAGGTCT | CTGCCAGGTC | TGATTGGATG | CCACAGGAAA | 960 |
| TCAGTCTATT | GGCATGTGAT | TGGAATGGGC | ACCACTCCTG | AAGTGCACTC | AATATTCCTC | 1020 |
| GAAGGTCACA | CATTTCTTGT | GAGGAACCAT | CGCCAGGCGT | CCTTGGAAAT | CTCGCCAATA | 1080 |
| ACTTTCCTTA | CTGCTCAAAC | ACTCTTGATG | GACCTTGGAC | AGTTTCTACT | GTTTTGTCAT | 1140 |
| ATCTCTTCCC | ACCAACATGA | TGGCATGGAA | GCTTATGTCA | AAGTAGACAG | CTGTCCAGAG | 1200 |
| GAACCCCAAC | TACGAATGAA | AAATAATGAA | GAAGCGGAAG | ACTATGATGA | TGATCTTACT | 1260 |
| GATTCTGAAA | TGGATGTGGT | CAGGTTTGAT | GATGACAACT | CTCCTTCCTT | TATCCAAATT | 1320 |
| CGCTCAGTTG | CCAAGAAGCA | TCCTAAAACT | TGGGTACATT | ACATTGCTGC | TGAAGAGGAG | 1380 |
| GACTGGGACT | ATGCTCCCTT | AGTCCTCGCC | CCCGATGACA | GAAGTTATAA | AAGTCAATAT | 1440 |
| TTGAACAATG | GCCCTCAGCG | GATTGGTAGG | AAGTACAAAA | AAGTCCGATT | TATGGCATAC | 1500 |
| ACAGATGAAA | CCTTTAAGAC | TCGTGAAGCT | ATTCAGCATG | AATCAGGAAT | CTTGGGACCT | 1560 |
| TTACTTTATG | GGGAAGTTGG | AGACACACTG | TTGATTATAT | TTAAGAATCA | AGCAAGCAGA | 1620 |
| CCATATAACA | TCTACCCTCA | CGGAATCACT | GATGTCCGTC | CTTTGTATTC | AAGGAGATTA | 1680 |
| CCAAAAGGTG | TAAAACATTT | GAAGGATTTT | CCAATTCTGC | CAGGAGAAAT | ATTCAAATAT | 1740 |
| AAATGGACAG | TGACTGTAGA | AGATGGGCCA | ACTAAATCAG | ATCCTCGGTG | CCTGACCCGC | 1800 |
| TATTACTCTA | GTTTCGTTAA | TATGGAGAGA | GATCTAGCTT | CAGGACTCAT | GGCCCTCTC | 1860 |
| CTCATCTGCT | ACAAAGAATC | TGTAGATCAA | AGAGGAAACC | AGATAATGTC | AGACAAGAGG | 1920 |
| AATGTCATCC | TGTTTTCTGT | ATTTGATGAG | AACCGAAGCT | GGTACCTCAC | AGAGAATATA | 1980 |
| CAACGCTTTC | TCCCCAATCC | AGCTGGAGTG | CAGCTTGAGG | ATCCAGAGTT | CCAAGCCTCC | 2040 |
| AACATCATGC | ACAGCATCAA | TGGCTATGTT | TTTGATAGTT | TGCAGTTGTC | AGTTTGTTTG | 2100 |
| CATGAGGTGG | CATACTGGTA | CATTCTAAGC | ATTGGAGCAC | AGACTGACTT | CCTTTCTGTC | 2160 |
| TTCTTCTCTG | GATATACCTT | CAAACACAAA | ATGGTCTATG | AAGACACACT | CACCCTATTC | 2220 |
| CCATTCTCAG | GAGAAACTGT | CTTCATGTCG | ATGGAAAACC | CAGGTCTATG | GATTCTGGGG | 2280 |

```
TGCCACAACT CAGACTTTCG GAACAGAGGC ATGACCGCCT TACTGAAGGT TTCTAGTTGT    2340
GACAAGAACA CTGGTGATTA TTACGAGGAC AGTTATGAAG ATATTTCAGC ATACTTGCTG    2400
AGTAAAAACA ATGCCATTGA ACCAAGAAGC TTCTCCCAGA ATTCAAGACA CCCTAGCACT    2460
AGGCAAAAGC AATTTAATGC CACCACAATT CCAGAAAATG ACATAGAGAA GACTGACCCT    2520
TGGTTTGCAC ACAGAACACC TATGCCTAAA ATACAAAATG TCTCCTCTAG TGATTTGTTG    2580
ATGCTCTTGC GACAGAGTCC TACTCCACAT GGGCTATCCT TATCTGATCT CCAAGAAGCC    2640
AAATATGAGA CTTTTTCTGA TGATCCATCA CCTGGAGCAA TAGACAGTAA TAACAGCCTG    2700
TCTGAAATGA CACACTTCAG GCCACAGCTC CATCACAGTG GGACATGGT ATTTACCCCT     2760
GAGTCAGGCC TCCAATTAAG ATTAAATGAG AAACTGGGGA CAACTGCAGC AACAGAGTTG    2820
AAGAAACTTG ATTTCAAAGT TTCTAGTACA TCAAATAATC TGATTTCAAC AATTCCATCA    2880
GACAATTTGG CAGCAGGTAC TGATAATACA AGTTCCTTAG ACCCCCAAG TATGCCAGTT     2940
CATTATGATA GTCAATTAGA TACCACTCTA TTTGGCAAAA AGTCATCTCC CCTTACTGAG    3000
TCTGGTGGAC CTCTGAGCTT GAGTGAAGAA ATAATGATT CAAAGTTGTT AGAATCAGGT     3060
TTAATGAATA GCCAAGAAAG TTCATGGGGA AAAAATGTAT CGTCAACAGA GAGTGGTAGG    3120
TTATTTAAAG GGAAAAGAGC TCATGGACCT GCTTTGTTGA CTAAAGATAA TGCCTTATTC    3180
AAAGTTAGCA TCTCTTTGTT AAAGACAAAC AAAACTTCCA ATAATTCAGC AACTAATAGA    3240
AAGACTCACA TTGATGGCCC ATCATTATTA ATTGAGAATA GTCCATCAGT CTGGCAAAAT    3300
ATATTAGAAA GTGACACTGA GTTTAAAAAA GTGACACCTT TGATTCATGA CAGAATGCTT    3360
ATGGACAAAA ATGCTACAGC TTTGAGGCTA AATCATATGT CAAATAAAAC TACTTCATCA    3420
AAAAACATGG AAATGGTCCA ACAGAAAAAA GAGGGCCCCA TTCCACCAGA TGCACAAAAT    3480
CCAGATATGT CGTTCTTTAA GATGCTATTC TTGCCAGAAT CAGCAAGGTG GATACAAAGG    3540
ACTCATGGAA AGAACTCTCT GAACTCTGGG CAAGGCCCCA GTCCAAAGCA ATTAGTATCC    3600
TTAGGACCAG AAAAATCTGT GGAAGGTCAG AATTTCTTGT CTGAGAAAAA CAAAGTGGTA    3660
GTAGGAAAGG GTGAATTTAC AAAGGACGTA GGACTCAAAG AGATGGTTTT TCCAAGCAGC    3720
AGAAACCTAT TTCTTACTAA CTTGGATAAT TTACATGAAA ATAATACACA CAATCAAGAA    3780
AAAAAAATTC AGGAAGAAAT AGAAAAGAAG GAAACATTAA TCCAAGAGAA TGTAGTTTTG    3840
CCTCAGATAC ATACAGTGAC TGGCACTAAG AATTTCATGA AGAACCTTTT CTTACTGAGC    3900
ACTAGGCAAA ATGTAGAAGG TTCATATGAG GGGGCATATG CTCCAGTACT TCAAGATTTT    3960
AGGTCATTAA ATGATTCAAC AAATAGAACA AGAAACACA CAGCTCATTT CTCAAAAAAA    4020
GGGGAGGAAG AAAACTTGGA AGGCTTGGGA AATCAAACCA AGCAAATTGT AGAGAAATAT    4080
GCATGCACCA CAAGGATATC TCCTAATACA AGCCAGCAGA ATTTGTCAC GCAACGTAGT     4140
AAGAGAGCTT TGAAACAATT CAGACTCCCA CTAGAAGAAA CAGAACTTGA AAAAAGGATA    4200
ATTGTGGATG ACACCTCAAC CCAGTGGTCC AAAAACATGA ACATTTGAC CCCGAGCACC     4260
CTCACACAGA TAGACTACAA TGAGAAGGAG AAAGGGGCCA TTACTCAGTC TCCCTTATCA    4320
GATTGCCTTA CGAGGAGTCA TAGCATCCCT CAAGCAAATA GATCTCCATT ACCCATTGCA    4380
AAGGTATCAT CATTTCCATC TATTAGACCT ATATATCTGA CCAGGGTCCT ATTCCAAGAC    4440
AACTCTTCTC ATCTTCCAGC AGCATCTTAT AGAAAGAAAG ATTCTGGGGT CCAAGAAAGC    4500
AGTCATTTCT TACAAGGAGC CAAAAAAAAT AACCTTTCTT TAGCCATTCT AACCTTGGAG    4560
ATGACTGGTG ATCAAAGAGA GGTTGGCTCC CTGGGGACAA GTGCCACAAA TTCAGTCACA    4620
TACAAGAAAG TTGAGAACAC TGTTCTCCCG AAACCAGACT TGCCCAAAAC ATCTGGCAAA    4680
```

```
GTTGAATTGC TTCCAAAAGT TCACATTTAT CAGAAGGACC TATTCCCTAC GGAAACTAGC    4740
AATGGGTCTC CTGGCCATCT GGATCTCGTG GAAGGGAGCC TTCTTCAGGG AACAGAGGGA    4800
GCGATTAAGT GGAATGAAGC AAACAGACCT GGAAAAGTTC CCTTTCTGAG AGTAGCAACA    4860
GAAAGCTCTG CAAAGACTCC CTCCAAGCTA TTGGATCCTC TTGCTTGGGA TAACCACTAT    4920
GGTACTCAGA TACCAAAAGA AGAGTGGAAA TCCCAAGAGA AGTCACCAGA AAAACAGCT     4980
TTTAAGAAAA AGGATACCAT TTTGTCCCTG AACGCTTGTG AAAGCAATCA TGCAATAGCA    5040
GCAATAAATG AGGGACAAAA TAAGCCCGAA ATAGAAGTCA CCTGGGCAAA GCAAGGTAGG    5100
ACTGAAAGGC TGTGCTCTCA AAACCCACCA GTCTTGAAAC GCCATCAACG GAAATAACT     5160
CGTACTACTC TTCAGTCAGA TCAAGAGGAA ATTGACTATG ATGATACCAT ATCAGTTGAA    5220
ATGAAGAAGG AAGATTTTGA CATTTATGAT GAGGATGAAA ATCAGAGCCC CGCAGCTTT     5280
CAAAAGAAAA CACGACACTA TTTTATTGCT GCAGTGGAGA GGCTCTGGGA TTATGGGATG    5340
AGTAGCTCCC CACATGTTCT AAGAAACAGG GCTCAGAGTG CAGTGTCCC  TCAGTTCAAG    5400
AAAGTTGTTT TCCAGGAATT TACTGATGGC TCCTTTACTC AGCCCTTATA CCGTGGAGAA    5460
CTAAATGAAC ATTTGGGACT CCTGGGGCCA TATATAAGAG CAGAAGTTGA AGATAATATC    5520
ATGGTAACTT TCAGAAATCA GGCCTCTCGT CCCTATTCCT TCTATTCTAG CCTTATTTCT    5580
TATGAGGAAG ATCAGAGGCA AGGAGCAGAA CCTAGAAAAA ACTTTGTCAA GCCTAATGAA    5640
ACCAAAACTT ACTTTTGGAA AGTGCAACAT CATATGGCAC CCACTAAAGA TGAGTTTGAC    5700
TGCAAAGCCT GGGCTTATTT CTCTGATGTT GACCTGGAAA AAGATGTGCA CTCAGGCCTG    5760
ATTGGACCCC TTCTGGTCTG CCACACTAAC ACACTGAACC CTGCTCATGG GAGACAAGTG    5820
ACAGTACAGG AATTTGCTCT GTTTTCACC  ATCTTTGATG AGACCAAAAG CTGGTACTTC    5880
ACTGAAAATA TGGAAAGAAA CTGCAGGGCT CCCTGCAATA TCCAGATGGA AGATCCCACT    5940
TTTAAAGAGA ATTATCGCTT CCATGCAATC AATGGCTACA TAATGGATAC ACTACCTGGC    6000
TTAGTAATGG CTCAGGATCA AAGGATTCGA TGGTATCTGC TCAGCATGGG CAGCAATGAA    6060
AACATCCATT CTATTCATTT CAGTGGACAT GTGTTCACTG TACGAAAAAA AGAGGAGTAT    6120
AAAATGGCAC TGTACAATCT CTATCCAGGT GTTTTTGAGA CAGTGGAAAT GTTACCATCC    6180
AAAGCTGGAA TTTGGCGGGT GGAATGCCTT ATTGGCGAGC ATCTACATGC TGGGATGAGC    6240
ACACTTTTTC TGGTGTACAG CAATAAGTGT CAGACTCCCC TGGGAATGGC TTCTGGACAC    6300
ATTAGAGATT TTCAGATTAC AGCTTCAGGA CAATATGGAC AGTGGGCCCC AAAGCTGGCC    6360
AGACTTCATT ATTCCGGATC AATCAATGCC TGGAGCACCA AGGAGCCCTT TTCTTGGATC    6420
AAGGTGGATC TGTTGGCACC AATGATTATT CACGGCATCA AGACCCAGGG TGCCCGTCAG    6480
AAGTTCTCCA GCCTCTACAT CTCTCAGTTT ATCATCATGT ATAGTCTTGA TGGGAAGAAG    6540
TGGCAGACTT ATCGAGGAAA TTCCACTGGA ACCTTAATGG TCTTCTTTGG CAATGTGGAT    6600
TCATCTGGGA TAAAACACAA TATTTTTAAC CCTCCAATTA TTGCTCGATA CATCCGTTTG    6660
CACCCAACTC ATTATAGCAT TCGCAGCACT CTTCGCATGG AGTTGATGGG CTGTGATTTA    6720
AATAGTTGCA GCATGCCATT GGGAATGGAG AGTAAAGCAA TATCAGATGC ACAGATTACT    6780
GCTTCATCCT ACTTTACCAA TATGTTTGCC ACCTGGTCTC CTTCAAAAGC TCGACTTCAC    6840
CTCCAAGGGA GGAGTAATGC CTGGAGACCT CAGGTGAATA ATCCAAAAGA GTGGCTGCAA    6900
GTGGACTTCC AGAAGACAAT GAAAGTCACA GGAGTAACTA CTCAGGGAGT AAAATCTCTG    6960
CTTACCAGCA TGTATGTGAA GGAGTTCCTC ATCTCCAGCA GTCAAGATGG CCATCAGTGG    7020
ACTCTCTTTT TTCAGAATGG CAAAGTAAAG GTTTTTCAGG GAAATCAAGA CTCCTTCACA    7080
```

| | | | | | | |
|---|---|---|---|---|---|---|
| CCTGTGGTGA | ACTCTCTAGA | CCCACCGTTA | CTGACTCGCT | ACCTTCGAAT | TCACCCCCAG | 7140 |
| AGTTGGGTGC | ACCAGATTGC | CCTGAGGATG | GAGGTTCTGG | GCTGCGAGGC | ACAGGACCTC | 7200 |
| TACTGAGGGT | GGCCACTGCA | GCACCTGCCA | CTGCCGTCAC | CTCTCCCTCC | TCAGCTCCAG | 7260 |
| GGCAGTGTCC | CTCCCTGGCT | TGCCTTCTAC | CTTTGTGCTA | AATCCTAGCA | GACACTGCCT | 7320 |
| TGAAGCCTCC | TGAATTAACT | ATCATCAGTC | CTGCATTTCT | TGGTGGGGG | GCCAGGAGGG | 7380 |
| TGCATCCAAT | TTAACTTAAC | TCTTACCTAT | TTTCTGCAGC | TGCTCCCAGA | TTACTCCTTC | 7440 |
| CTTCCAATAT | AACTAGGCAA | AAGAAGTGA | GGAGAAACCT | GCATGAAAGC | ATTCTTCCCT | 7500 |
| GAAAAGTTAG | GCCTCTCAGA | GTCACCACTT | CCTCTGTTGT | AGAAAAACTA | TGTGATGAAA | 7560 |
| CTTTGAAAAA | GATATTTATG | ATGTTAACAT | TCAGGTTAA | GCCTCATACG | TTTAAAATAA | 7620 |
| AACTCTCAGT | TGTTTATTAT | CCTGATCAAG | CATGGAACAA | AGCATGTTTC | AGGATCAGAT | 7680 |
| CAATACAATC | TTGGAGTCAA | AAGGCAAATC | ATTTGGACAA | TCTGCAAAAT | GGAGAGAATA | 7740 |
| CAATAACTAC | TACAGTAAAG | TCTGTTTCTG | CTTCCTTACA | CATAGATATA | ATTATGTTAT | 7800 |
| TTAGTCATTA | TGAGGGGCAC | ATTCTTATCT | CCAAAACTAG | CATTCTTAAA | CTGAGAATTA | 7860 |
| TAGATGGGGT | TCAAGAATCC | CTAAGTCCCC | TGAAATTATA | TAAGGCATTC | TGTATAAATG | 7920 |
| CAAATGTGCA | TTTTTCTGAC | GAGTGTCCAT | AGATATAAAG | CCATTGGTCT | TAATTCTGAC | 7980 |
| CAATAAAAAA | ATAAGTCAGG | AGGATGCAAT | TGTTGAAAGC | TTTGAAATAA | AATAACATGT | 8040 |
| CTTCTTGAAA | TTTGTGATGG | CCAAGAAAGA | AAATGATGAT | GACATTAGGC | TTCTAAAGGA | 8100 |
| CATACATTTA | ATATTTCTGT | GGAAATATGA | GGAAATCCA | TGGTTATCTG | AGATAGGAGA | 8160 |
| TACAAACTTT | GTAATTCTAA | TAATGCACTC | AGTTACTCT | CTCCCTCTAC | TAATTTCCTG | 8220 |
| CTGAAAATAA | CACAACAAAA | ATGTAACAGG | GGAAATTATA | TACCGTGACT | GAAAACTAGA | 8280 |
| GTCCTACTTA | CATAGTTGAA | ATATCAAGGA | GGTCAGAAGA | AAATTGGACT | GGTGAAAACA | 8340 |
| GAAAAAACAC | TCCAGTCTGC | CATATCACCA | CACAATAGGA | TCCCCCTTCT | TGCCCTCCAC | 8400 |
| CCCCATAAGA | TTGTGAAGGG | TTTACTGCTC | CTTCCATCTG | CCTGCACCCC | TTCACTATGA | 8460 |
| CTACACAGAA | CTCTCCTGAT | AGTAAGGGG | GCTGGAGGCA | AGGATAAGTT | ATAGAGCAGT | 8520 |
| TGGAGGAAGC | ATCCAAAGAC | TGCAACCCAG | GGCAAATGGA | AAACAGGAGA | TCCTAATATG | 8580 |
| AAAGAAAAAT | GGATCCCAAT | CTGAGAAAAG | GCAAAGAAT | GGCTACTTTT | TTCTATGCTG | 8640 |
| GAGTATTTTC | TAATAATCCT | GCTTGACCCT | TATCTGACCT | CTTTGGAAAC | TATAACATAG | 8700 |
| CTGTCACAGT | ATAGTCACAA | TCCACAAATG | ATGCAGGTGC | AAATGGTTTA | TAGCCCTGTG | 8760 |
| AAGTTCTTAA | AGTTTAGAGG | CTAACTTACA | GAAATGAATA | AGTTGTTTG | TTTTATAGCC | 8820 |
| CGGTAGAGGA | GTTAACCCCA | AAGGTGATAT | GGTTTTATTT | CCTGTTATGT | TTAACTTGAT | 8880 |
| AATCTTATTT | TGGCATTCTT | TTCCCATTGA | CTATATACAT | CTCTATTTCT | CAAATGTTCA | 8940 |
| TGGAACTAGC | TCTTTTATTT | TCCTGCTGGT | TTCTTCAGTA | ATGAGTTAAA | TAAAACATTG | 9000 |
| ACACATACA | | | | | | 9009 |

( 2 ) INFORMATION FOR SEQ ID NO:2:

( i ) SEQUENCE CHARACTERISTICS:
        ( A ) LENGTH: 2332 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO (v) FRAGMENT TYPE: N-terminal (vi) ORIGINAL SOURCE:
    (A) ORGANISM: Homo sapien
    (F) TISSUE TYPE: Liver cDNA sequence (xi) SEQUENCE DESCRIPTION: SEQ ID NO:2:

```
Ala Thr Arg Arg Tyr Tyr Leu Gly Ala Val Glu Leu Ser Trp Asp Tyr
 1               5                  10                  15
Met Gln Ser Asp Leu Gly Glu Leu Pro Val Asp Ala Arg Phe Pro Pro
            20                  25                  30
Arg Val Pro Lys Ser Phe Pro Phe Asn Thr Ser Val Val Tyr Lys Lys
        35                  40                  45
Thr Leu Phe Val Glu Phe Thr Val His Leu Phe Asn Ile Ala Lys Pro
    50                  55                  60
Arg Pro Pro Trp Met Gly Leu Leu Gly Pro Thr Ile Gln Ala Glu Val
65                  70                  75                  80
Tyr Asp Thr Val Val Ile Thr Leu Lys Asn Met Ala Ser His Pro Val
                85                  90                  95
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
        115                 120                 125
Phe Pro Gly Gly Ser His Thr Tyr Val Trp Gln Val Leu Lys Glu Asn
    130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
```

| Tyr | Ile | Ala | Ala | Glu | Glu | Glu | Asp | Trp | Asp | Tyr | Ala | Pro | Leu | Val | Leu |
|---|---|---|---|---|---|---|---|---|---|---|---|---|---|---|---|
| 385 | | | | 390 | | | | 395 | | | | | | | 400 |

| Ala | Pro | Asp | Asp | Arg | Ser | Tyr | Lys | Ser | Gln | Tyr | Leu | Asn | Asn | Gly | Pro |
|---|---|---|---|---|---|---|---|---|---|---|---|---|---|---|---|
| | | | | 405 | | | | | 410 | | | | | 415 | |

| Gln | Arg | Ile | Gly | Arg | Lys | Tyr | Lys | Lys | Val | Arg | Phe | Met | Ala | Tyr | Thr |
|---|---|---|---|---|---|---|---|---|---|---|---|---|---|---|---|
| | | | 420 | | | | | 425 | | | | | 430 | | |

| Asp | Glu | Thr | Phe | Lys | Thr | Arg | Glu | Ala | Ile | Gln | His | Glu | Ser | Gly | Ile |
|---|---|---|---|---|---|---|---|---|---|---|---|---|---|---|---|
| | | 435 | | | | | 440 | | | | | 445 | | | |

| Leu | Gly | Pro | Leu | Leu | Tyr | Gly | Glu | Val | Gly | Asp | Thr | Leu | Leu | Ile | Ile |
|---|---|---|---|---|---|---|---|---|---|---|---|---|---|---|---|
| | 450 | | | | | 455 | | | | | 460 | | | | |

| Phe | Lys | Asn | Gln | Ala | Ser | Arg | Pro | Tyr | Asn | Ile | Tyr | Pro | His | Gly | Ile |
|---|---|---|---|---|---|---|---|---|---|---|---|---|---|---|---|
| 465 | | | | | 470 | | | | | 475 | | | | | 480 |

| Thr | Asp | Val | Arg | Pro | Leu | Tyr | Ser | Arg | Arg | Leu | Pro | Lys | Gly | Val | Lys |
|---|---|---|---|---|---|---|---|---|---|---|---|---|---|---|---|
| | | | | 485 | | | | | 490 | | | | | 495 | |

| His | Leu | Lys | Asp | Phe | Pro | Ile | Leu | Pro | Gly | Glu | Ile | Phe | Lys | Tyr | Lys |
|---|---|---|---|---|---|---|---|---|---|---|---|---|---|---|---|
| | | | 500 | | | | 505 | | | | | 510 | | | |

| Trp | Thr | Val | Thr | Val | Glu | Asp | Gly | Pro | Thr | Lys | Ser | Asp | Pro | Arg | Cys |
|---|---|---|---|---|---|---|---|---|---|---|---|---|---|---|---|
| | | 515 | | | | | 520 | | | | | 525 | | | |

| Leu | Thr | Arg | Tyr | Tyr | Ser | Ser | Phe | Val | Asn | Met | Glu | Arg | Asp | Leu | Ala |
|---|---|---|---|---|---|---|---|---|---|---|---|---|---|---|---|
| | 530 | | | | | 535 | | | | | 540 | | | | |

| Ser | Gly | Leu | Ile | Gly | Pro | Leu | Leu | Ile | Cys | Tyr | Lys | Glu | Ser | Val | Asp |
|---|---|---|---|---|---|---|---|---|---|---|---|---|---|---|---|
| 545 | | | | | 550 | | | | | 555 | | | | | 560 |

| Gln | Arg | Gly | Asn | Gln | Ile | Met | Ser | Asp | Lys | Arg | Asn | Val | Ile | Leu | Phe |
|---|---|---|---|---|---|---|---|---|---|---|---|---|---|---|---|
| | | | | 565 | | | | | 570 | | | | | 575 | |

| Ser | Val | Phe | Asp | Glu | Asn | Arg | Ser | Trp | Tyr | Leu | Thr | Glu | Asn | Ile | Gln |
|---|---|---|---|---|---|---|---|---|---|---|---|---|---|---|---|
| | | | 580 | | | | | 585 | | | | | 590 | | |

| Arg | Phe | Leu | Pro | Asn | Pro | Ala | Gly | Val | Gln | Leu | Glu | Asp | Pro | Glu | Phe |
|---|---|---|---|---|---|---|---|---|---|---|---|---|---|---|---|
| | | 595 | | | | | 600 | | | | | 605 | | | |

| Gln | Ala | Ser | Asn | Ile | Met | His | Ser | Ile | Asn | Gly | Tyr | Val | Phe | Asp | Ser |
|---|---|---|---|---|---|---|---|---|---|---|---|---|---|---|---|
| | 610 | | | | | 615 | | | | | 620 | | | | |

| Leu | Gln | Leu | Ser | Val | Cys | Leu | His | Glu | Val | Ala | Tyr | Trp | Tyr | Ile | Leu |
|---|---|---|---|---|---|---|---|---|---|---|---|---|---|---|---|
| 625 | | | | | 630 | | | | | 635 | | | | | 640 |

| Ser | Ile | Gly | Ala | Gln | Thr | Asp | Phe | Leu | Ser | Val | Phe | Phe | Ser | Gly | Tyr |
|---|---|---|---|---|---|---|---|---|---|---|---|---|---|---|---|
| | | | | 645 | | | | | 650 | | | | | 655 | |

| Thr | Phe | Lys | His | Lys | Met | Val | Tyr | Glu | Asp | Thr | Leu | Thr | Leu | Phe | Pro |
|---|---|---|---|---|---|---|---|---|---|---|---|---|---|---|---|
| | | | 660 | | | | | 665 | | | | | 670 | | |

| Phe | Ser | Gly | Glu | Thr | Val | Phe | Met | Ser | Met | Glu | Asn | Pro | Gly | Leu | Trp |
|---|---|---|---|---|---|---|---|---|---|---|---|---|---|---|---|
| | | 675 | | | | | 680 | | | | | 685 | | | |

| Ile | Leu | Gly | Cys | His | Asn | Ser | Asp | Phe | Arg | Asn | Arg | Gly | Met | Thr | Ala |
|---|---|---|---|---|---|---|---|---|---|---|---|---|---|---|---|
| | 690 | | | | | 695 | | | | | 700 | | | | |

| Leu | Leu | Lys | Val | Ser | Ser | Cys | Asp | Lys | Asn | Thr | Gly | Asp | Tyr | Tyr | Glu |
|---|---|---|---|---|---|---|---|---|---|---|---|---|---|---|---|
| 705 | | | | | 710 | | | | | 715 | | | | | 720 |

| Asp | Ser | Tyr | Glu | Asp | Ile | Ser | Ala | Tyr | Leu | Leu | Ser | Lys | Asn | Asn | Ala |
|---|---|---|---|---|---|---|---|---|---|---|---|---|---|---|---|
| | | | | 725 | | | | | 730 | | | | | 735 | |

| Ile | Glu | Pro | Arg | Ser | Phe | Ser | Gln | Asn | Ser | Arg | His | Pro | Ser | Thr | Arg |
|---|---|---|---|---|---|---|---|---|---|---|---|---|---|---|---|
| | | | 740 | | | | | 745 | | | | | 750 | | |

| Gln | Lys | Gln | Phe | Asn | Ala | Thr | Thr | Ile | Pro | Glu | Asn | Asp | Ile | Glu | Lys |
|---|---|---|---|---|---|---|---|---|---|---|---|---|---|---|---|
| | | 755 | | | | | 760 | | | | | 765 | | | |

| Thr | Asp | Pro | Trp | Phe | Ala | His | Arg | Thr | Pro | Met | Pro | Lys | Ile | Gln | Asn |
|---|---|---|---|---|---|---|---|---|---|---|---|---|---|---|---|
| | 770 | | | | | 775 | | | | | 780 | | | | |

| Val | Ser | Ser | Ser | Asp | Leu | Leu | Met | Leu | Leu | Arg | Gln | Ser | Pro | Thr | Pro |
|---|---|---|---|---|---|---|---|---|---|---|---|---|---|---|---|
| 785 | | | | | 790 | | | | | 795 | | | | | 800 |

| His | Gly | Leu | Ser | Leu | Ser | Asp | Leu | Gln | Glu | Ala | Lys | Tyr | Glu | Thr | Phe |
|---|---|---|---|---|---|---|---|---|---|---|---|---|---|---|---|

|     |     |     | 805 |     |     |     | 810 |     |     |     | 815 |     |     |
|-----|-----|-----|-----|-----|-----|-----|-----|-----|-----|-----|-----|-----|-----|

Ser Asp Asp Pro Ser Pro Gly Ala Ile Asp Ser Asn Asn Ser Leu Ser
        820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                     855                 860

Thr Thr Ala Ala Thr Glu Leu Lys Lys Leu Asp Phe Lys Val Ser Ser
865                 870                  875                     880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                  955                     960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu Asn
        1010                1015                1020

Ser Pro Ser Val Trp Gln Asn Ile Leu Glu Ser Asp Thr Glu Phe Lys
1025                1030                1035                    1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
        1075                1080                1085

Ala Gln Asn Pro Asp Met Ser Phe Phe Lys Met Leu Phe Leu Pro Glu
    1090                1095                1100

Ser Ala Arg Trp Ile Gln Arg Thr His Gly Lys Asn Ser Leu Asn Ser
1105                1110                1115                    1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
            1140                1145                1150

Gly Lys Gly Glu Phe Thr Lys Asp Val Gly Leu Lys Glu Met Val Phe
            1155                1160                1165

Pro Ser Ser Arg Asn Leu Phe Leu Thr Asn Leu Asp Asn Leu His Glu
    1170                1175                1180

Asn Asn Thr His Asn Gln Glu Lys Lys Ile Gln Glu Glu Ile Glu Lys
1185                1190                1195                    1200

Lys Glu Thr Leu Ile Gln Glu Asn Val Val Leu Pro Gln Ile His Thr
            1205                1210                1215

Val Thr Gly Thr Lys Asn Phe Met Lys Asn Leu Phe Leu Leu Ser Thr
            1220                1225                1230

```
Arg Gln Asn Val Glu Gly Ser Tyr Glu Gly Ala Tyr Ala Pro Val Leu
        1235                1240                1245
Gln Asp Phe Arg Ser Leu Asn Asp Ser Thr Asn Arg Thr Lys Lys His
        1250                1255                1260
Thr Ala His Phe Ser Lys Lys Gly Glu Glu Asn Leu Glu Gly Leu
1265                1270                1275                1280
Gly Asn Gln Thr Lys Gln Ile Val Glu Lys Tyr Ala Cys Thr Thr Arg
                1285                1290                1295
Ile Ser Pro Asn Thr Ser Gln Gln Asn Phe Val Thr Gln Arg Ser Lys
                1300                1305                1310
Arg Ala Leu Lys Gln Phe Arg Leu Pro Leu Glu Glu Thr Glu Leu Glu
        1315                1320                1325
Lys Arg Ile Ile Val Asp Asp Thr Ser Thr Gln Trp Ser Lys Asn Met
        1330                1335                1340
Lys His Leu Thr Pro Ser Thr Leu Thr Gln Ile Asp Tyr Asn Glu Lys
1345                1350                1355                1360
Glu Lys Gly Ala Ile Thr Gln Ser Pro Leu Ser Asp Cys Leu Thr Arg
                1365                1370                1375
Ser His Ser Ile Pro Gln Ala Asn Arg Ser Pro Leu Pro Ile Ala Lys
                1380                1385                1390
Val Ser Ser Phe Pro Ser Ile Arg Pro Ile Tyr Leu Thr Arg Val Leu
        1395                1400                1405
Phe Gln Asp Asn Ser Ser His Leu Pro Ala Ala Ser Tyr Arg Lys Lys
        1410                1415                1420
Asp Ser Gly Val Gln Glu Ser Ser His Phe Leu Gln Gly Ala Lys Lys
1425                1430                1435                1440
Asn Asn Leu Ser Leu Ala Ile Leu Thr Leu Glu Met Thr Gly Asp Gln
                1445                1450                1455
Arg Glu Val Gly Ser Leu Gly Thr Ser Ala Thr Asn Ser Val Thr Tyr
        1460                1465                1470
Lys Lys Val Glu Asn Thr Val Leu Pro Lys Pro Asp Leu Pro Lys Thr
        1475                1480                1485
Ser Gly Lys Val Glu Leu Leu Pro Lys Val His Ile Tyr Gln Lys Asp
        1490                1495                1500
Leu Phe Pro Thr Glu Thr Ser Asn Gly Ser Pro Gly His Leu Asp Leu
1505                1510                1515                1520
Val Glu Gly Ser Leu Leu Gln Gly Thr Glu Gly Ala Ile Lys Trp Asn
                1525                1530                1535
Glu Ala Asn Arg Pro Gly Lys Val Pro Phe Leu Arg Val Ala Thr Glu
        1540                1545                1550
Ser Ser Ala Lys Thr Pro Ser Lys Leu Leu Asp Pro Leu Ala Trp Asp
        1555                1560                1565
Asn His Tyr Gly Thr Gln Ile Pro Lys Glu Glu Trp Lys Ser Gln Glu
        1570                1575                1580
Lys Ser Pro Glu Lys Thr Ala Phe Lys Lys Lys Asp Thr Ile Leu Ser
1585                1590                1595                1600
Leu Asn Ala Cys Glu Ser Asn His Ala Ile Ala Ala Ile Asn Glu Gly
                1605                1610                1615
Gln Asn Lys Pro Glu Ile Glu Val Thr Trp Ala Lys Gln Gly Arg Thr
        1620                1625                1630
Glu Arg Leu Cys Ser Gln Asn Pro Pro Val Leu Lys Arg His Gln Arg
        1635                1640                1645
Glu Ile Thr Arg Thr Thr Leu Gln Ser Asp Gln Glu Glu Ile Asp Tyr
        1650                1655                1660
```

```
Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
            1700                1705                1710

Ser Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Arg Lys Asn Phe Val Lys
        1795                1800                1805

Pro Asn Glu Thr Lys Thr Tyr Phe Trp Lys Val Gln His His Met Ala
1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
        2035                2040                2045

Lys Leu Ala Arg Leu His Tyr Ser Gly Ser Ile Asn Ala Trp Ser Thr
    2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
```

|  |  |  |  |  | 2085 |  |  |  |  | 2090 |  |  |  |  | 2095 |
|---|---|---|---|---|---|---|---|---|---|---|---|---|---|---|---|

Tyr Ile Ser Gln Phe Ile Ile Met Tyr Ser Leu Asp Gly Lys Lys Trp
            2100                            2105                      2110

Gln Thr Tyr Arg Gly Asn Ser Thr Gly Thr Leu Met Val Phe Phe Gly
            2115                            2120                      2125

Asn Val Asp Ser Ser Gly Ile Lys His Asn Ile Phe Asn Pro Pro Ile
            2130                            2135                      2140

Ile Ala Arg Tyr Ile Arg Leu His Pro Thr His Tyr Ser Ile Arg Ser
2145                      2150                      2155                      2160

Thr Leu Arg Met Glu Leu Met Gly Cys Asp Leu Asn Ser Cys Ser Met
            2165                            2170                      2175

Pro Leu Gly Met Glu Ser Lys Ala Ile Ser Asp Ala Gln Ile Thr Ala
            2180                            2185                      2190

Ser Ser Tyr Phe Thr Asn Met Phe Ala Thr Trp Ser Pro Ser Lys Ala
            2195                            2200                      2205

Arg Leu His Leu Gln Gly Arg Ser Asn Ala Trp Arg Pro Gln Val Asn
            2210                            2215                      2220

Asn Pro Lys Glu Trp Leu Gln Val Asp Phe Gln Lys Thr Met Lys Val
2225                      2230                      2235                      2240

Thr Gly Val Thr Thr Gln Gly Val Lys Ser Leu Leu Thr Ser Met Tyr
            2245                            2250                      2255

Val Lys Glu Phe Leu Ile Ser Ser Ser Gln Asp Gly His Gln Trp Thr
            2260                            2265                      2270

Leu Phe Phe Gln Asn Gly Lys Val Lys Val Phe Gln Gly Asn Gln Asp
            2275                            2280                      2285

Ser Phe Thr Pro Val Val Asn Ser Leu Asp Pro Pro Leu Leu Thr Arg
            2290                            2295                      2300

Tyr Leu Arg Ile His Pro Gln Ser Trp Val His Gln Ile Ala Leu Arg
2305                      2310                      2315                      2320

Met Glu Val Leu Gly Cys Glu Ala Gln Asp Leu Tyr
            2325                            2330

( 2 ) INFORMATION FOR SEQ ID NO:3:

( i ) SEQUENCE CHARACTERISTICS:
        ( A ) LENGTH: 868 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Porcine ( i x ) FEATURE:
        ( A ) NAME/KEY: Protein
        ( B ) LOCATION: 1..868
        ( D ) OTHER INFORMATION: /note= "Predicted amino acid
            sequence of the B and part of the A2 domains of
            porcine factor VIII."

( x i ) SEQUENCE DESCRIPTION: SEQ ID NO:3:

Gly Leu Trp Val Leu Gly Cys His Met Ser Asp Leu Arg Asn Arg Gly
1                      5                      10                      15

Met Thr Ala Leu Leu Lys Val Tyr Ser Cys Asp Arg Asp Thr Gly Asp

-continued

|  |  |  | 20 |  |  |  | 25 |  |  |  | 30 |  |  |  |
|---|---|---|---|---|---|---|---|---|---|---|---|---|---|---|
| Tyr | Tyr | Asp | Asn | Thr | Tyr | Glu | Asp | Leu | Pro | Gly | Phe | Leu | Leu | Ser | Gly |
|  |  |  | 35 |  |  |  | 40 |  |  |  | 45 |  |  |  |
| Lys | Asn | Val | Ile | Glu | Pro | Arg | Ser | Phe | Ala | Gln | Asn | Ser | Arg | Pro | Pro |
|  |  |  | 50 |  |  |  | 55 |  |  |  | 60 |  |  |  |
| Ser | Ala | Ser | Gln | Lys | Gln | Phe | Gln | Thr | Ile | Thr | Ser | Pro | Glu | Asp | Asp |
| 65 |  |  |  |  |  | 70 |  |  |  | 75 |  |  |  |  | 80 |
| Val | Glu | Leu | Asp | Pro | Gln | Ser | Gln | Glu | Arg | Thr | Gln | Ala | Leu | Glu | Glu |
|  |  |  |  | 85 |  |  |  |  | 90 |  |  |  |  | 95 |  |
| Leu | Ser | Val | Pro | Ser | Gly | Asp | Gly | Ser | Met | Leu | Leu | Gly | Gln | Asn | Pro |
|  |  |  | 100 |  |  |  |  | 105 |  |  |  |  | 110 |  |  |
| Ala | Pro | His | Gly | Ser | Ser | Ser | Ser | Asp | Leu | Gln | Glu | Ala | Arg | Asn | Glu |
|  |  |  | 115 |  |  |  |  | 120 |  |  |  |  | 125 |  |  |
| Ala | Asp | Asp | Tyr | Leu | Pro | Gly | Ala | Arg | Glu | Arg | Asn | Thr | Ala | Pro | Ser |
|  |  |  | 130 |  |  |  |  | 135 |  |  |  |  | 140 |  |  |
| Ala | Ala | Ala | Arg | Leu | Arg | Pro | Glu | Leu | His | His | Ser | Ala | Glu | Arg | Val |
| 145 |  |  |  |  |  | 150 |  |  |  | 155 |  |  |  |  | 160 |
| Leu | Thr | Pro | Glu | Pro | Glu | Lys | Glu | Leu | Lys | Lys | Leu | Asp | Ser | Lys | Met |
|  |  |  |  | 165 |  |  |  |  | 170 |  |  |  |  | 175 |  |
| Ser | Ser | Ser | Ser | Asp | Leu | Leu | Lys | Thr | Ser | Pro | Thr | Ile | Pro | Ser | Asp |
|  |  |  | 180 |  |  |  |  | 185 |  |  |  |  | 190 |  |  |
| Thr | Leu | Ser | Ala | Glu | Thr | Glu | Arg | Thr | His | Ser | Leu | Gly | Pro | Pro | His |
|  |  |  | 195 |  |  |  |  | 200 |  |  |  |  | 205 |  |  |
| Pro | Gln | Val | Asn | Phe | Arg | Ser | Gln | Leu | Gly | Ala | Ile | Val | Leu | Gly | Lys |
|  |  |  | 210 |  |  |  |  | 215 |  |  |  |  | 220 |  |  |
| Asn | Ser | Ser | His | Phe | Ile | Gly | Ala | Gly | Val | Pro | Leu | Gly | Ser | Thr | Glu |
| 225 |  |  |  |  |  | 230 |  |  |  | 235 |  |  |  |  | 240 |
| Phe | Asp | His | Glu | Ser | Ser | Leu | Gly | Glu | Asn | Val | Ser | Pro | Val | Glu | Ser |
|  |  |  |  | 245 |  |  |  |  | 250 |  |  |  |  | 255 |  |
| Asp | Gly | Ile | Phe | Glu | Lys | Glu | Arg | Ala | His | Gly | Pro | Ala | Ser | Leu | Thr |
|  |  |  | 260 |  |  |  |  | 265 |  |  |  |  | 270 |  |  |
| Lys | Asp | Asp | Val | Leu | Phe | Lys | Val | Asn | Ile | Ser | Leu | Val | Lys | Thr | Asn |
|  |  |  | 275 |  |  |  |  | 280 |  |  |  |  | 285 |  |  |
| Lys | Ala | Arg | Val | Tyr | Leu | Lys | Thr | Asn | Arg | Lys | Ile | His | Ile | Asp | Asp |
|  |  |  | 290 |  |  |  |  | 295 |  |  |  |  | 300 |  |  |
| Ala | Ala | Leu | Leu | Thr | Glu | Asn | Arg | Ala | Ser | Ala | Thr | Phe | Met | Asp | Lys |
| 305 |  |  |  |  |  | 310 |  |  |  | 315 |  |  |  |  | 320 |
| Asn | Thr | Thr | Ala | Ser | Gly | Leu | Asn | His | Val | Ser | Asn | Trp | Ile | Lys | Gly |
|  |  |  |  | 325 |  |  |  |  | 330 |  |  |  |  | 335 |  |
| Pro | Leu | Gly | Lys | Asn | Pro | Leu | Ser | Ser | Glu | Arg | Gly | Pro | Ser | Pro | Glu |
|  |  |  | 340 |  |  |  |  | 345 |  |  |  |  | 350 |  |  |
| Leu | Leu | Thr | Ser | Ser | Gly | Ser | Gly | Lys | Ser | Val | Lys | Gly | Gln | Ser | Ser |
|  |  |  | 355 |  |  |  |  | 360 |  |  |  |  | 365 |  |  |
| Gly | Gln | Gly | Arg | Ile | Arg | Val | Ala | Val | Glu | Glu | Glu | Leu | Ser | Lys |  |
|  |  |  | 370 |  |  |  |  | 375 |  |  |  |  | 380 |  |  |
| Gly | Lys | Glu | Met | Met | Leu | Pro | Asn | Ser | Glu | Leu | Thr | Phe | Leu | Thr | Asn |
| 385 |  |  |  |  |  | 390 |  |  |  | 395 |  |  |  |  | 400 |
| Ser | Ala | Asp | Val | Gln | Gly | Asn | Asp | Thr | His | Ser | Gln | Gly | Lys | Lys | Ser |
|  |  |  |  | 405 |  |  |  |  | 410 |  |  |  |  | 415 |  |
| Arg | Glu | Glu | Met | Glu | Arg | Arg | Glu | Leu | Val | Gln | Glu | Lys | Val | Asp | Leu |
|  |  |  | 420 |  |  |  |  | 425 |  |  |  |  | 430 |  |  |
| Pro | Gln | Val | Tyr | Thr | Ala | Thr | Gly | Thr | Lys | Asn | Phe | Leu | Arg | Asn | Ile |
|  |  |  | 435 |  |  |  |  | 440 |  |  |  |  | 445 |  |  |

| | | | | | | | | | | | | | | |
|---|---|---|---|---|---|---|---|---|---|---|---|---|---|---|
| Phe | His | Gln | Ser | Thr | Glu | Pro | Ser | Val | Glu | Gly | Phe | Asp | Gly | Gly | Ser |
| | 450 | | | | | 455 | | | | | 460 | | | |
| His | Ala | Pro | Val | Pro | Gln | Asp | Ser | Arg | Ser | Leu | Asn | Asp | Ser | Ala | Glu |
| 465 | | | | | 470 | | | | | 475 | | | | | 480 |
| Arg | Ala | Glu | Thr | His | Ile | Ala | His | Phe | Ser | Ala | Ile | Arg | Glu | Glu | Ala |
| | | | | 485 | | | | | 490 | | | | | 495 | |
| Pro | Leu | Glu | Ala | Pro | Gly | Asn | Phe | Thr | Gly | Pro | Gly | Pro | Arg | Ser | Ala |
| | | | | 500 | | | | | 505 | | | | 510 | | |
| Val | Pro | Arg | Arg | Val | Lys | Gln | Ser | Leu | Lys | Gln | Ile | Arg | Leu | Pro | Leu |
| | | | 515 | | | | | 520 | | | | | 525 | | |
| Glu | Glu | Ile | Lys | Pro | Glu | Arg | Gly | Val | Val | Leu | Asn | Ala | Thr | Ser | Thr |
| | | 530 | | | | 535 | | | | | 540 | | | | |
| Arg | Trp | Ser | Glu | Ser | Ser | Pro | Ile | Leu | Gln | Gly | Ala | Lys | Arg | Asn | Asn |
| 545 | | | | | 550 | | | | | 555 | | | | | 560 |
| Leu | Ser | Leu | Pro | Phe | Leu | Thr | Leu | Glu | Met | Ala | Gly | Gly | Gln | Gly | Lys |
| | | | | 565 | | | | | 570 | | | | | 575 | |
| Ile | Ser | Ala | Leu | Gly | Lys | Ser | Ala | Ala | Gly | Pro | Leu | Ala | Ser | Gly | Lys |
| | | | 580 | | | | | 585 | | | | | 590 | | |
| Leu | Glu | Lys | Ala | Val | Leu | Ser | Ser | Ala | Gly | Leu | Ser | Glu | Ala | Ser | Gly |
| | | 595 | | | | | 600 | | | | | 605 | | | |
| Lys | Ala | Glu | Phe | Leu | Pro | Lys | Val | Arg | Val | His | Arg | Glu | Asp | Leu | Leu |
| | 610 | | | | | 615 | | | | | 620 | | | | |
| Pro | Gln | Lys | Thr | Ser | Asn | Val | Ser | Cys | Ala | His | Gly | Asp | Ile | Gly | Gln |
| 625 | | | | | 630 | | | | | 635 | | | | | 640 |
| Glu | Ile | Phe | Leu | Gln | Lys | Thr | Arg | Gly | Pro | Val | Asn | Leu | Asn | Lys | Val |
| | | | | 645 | | | | | 650 | | | | | 655 | |
| Asn | Arg | Pro | Gly | Arg | Thr | Pro | Ser | Lys | Leu | Leu | Gly | Pro | Pro | Met | Pro |
| | | | 660 | | | | | 665 | | | | | 670 | | |
| Lys | Glu | Trp | Glu | Ser | Leu | Glu | Lys | Ser | Pro | Lys | Ser | Thr | Ala | Leu | Arg |
| | | 675 | | | | | 680 | | | | | 685 | | | |
| Thr | Lys | Asp | Ile | Leu | Ser | Leu | Pro | Leu | Asp | Arg | His | Glu | Ser | Asn | His |
| | 690 | | | | | 695 | | | | | 700 | | | | |
| Ser | Ile | Ala | Ala | Lys | Asn | Glu | Gly | Gln | Ala | Phe | Thr | Gln | Arg | Glu | Ala |
| 705 | | | | | 710 | | | | | 715 | | | | | 720 |
| Ala | Trp | Thr | Lys | Gln | Gly | Gly | Pro | Gly | Arg | Leu | Cys | Ala | Pro | Lys | Pro |
| | | | | 725 | | | | | 730 | | | | | 735 | |
| Pro | Val | Leu | Arg | Arg | His | Gln | Arg | Asp | Ile | Ser | Leu | Pro | Thr | Pro | Gln |
| | | | 740 | | | | | 745 | | | | | 750 | | |
| Pro | Glu | Glu | Asp | Lys | Met | Asp | Tyr | Asp | Asp | Ile | Phe | Ser | Thr | Glu | Thr |
| | | 755 | | | | | 760 | | | | | 765 | | | |
| Lys | Gly | Glu | Asp | Phe | Asp | Ile | Tyr | Gly | Glu | Asp | Asn | Gln | Asp | Pro |
| | 770 | | | | | 775 | | | | | 780 | | | | |
| Arg | Ser | Phe | Gln | Lys | Arg | Thr | Arg | His | Tyr | Phe | Ile | Ala | Ala | Val | Glu |
| 785 | | | | | 790 | | | | | 795 | | | | | 800 |
| Gln | Leu | Trp | Asp | Tyr | Gly | Met | Ser | Glu | Ser | Pro | Arg | Ala | Leu | Arg | Asn |
| | | | | 805 | | | | | 810 | | | | | 815 | |
| Arg | Ala | Gln | Asn | Gly | Glu | Val | Pro | Arg | Phe | Lys | Lys | Val | Val | Phe | Arg |
| | | | 820 | | | | | 825 | | | | | 830 | | |
| Glu | Phe | Ala | Asp | Gly | Ser | Phe | Thr | Asn | Pro | Ser | Tyr | Arg | Gly | Glu | Leu |
| | | 835 | | | | | 840 | | | | | 845 | | | |
| Asn | Lys | His | Leu | Gly | Leu | Leu | Gly | Pro | Tyr | Ile | Arg | Ala | Glu | Val | Glu |
| | 850 | | | | | 855 | | | | | 860 | | | | |
| Asp | Asn | Ile | Met | | | | | | | | | | | | |
| 865 | | | | | | | | | | | | | | | |

( 2 ) INFORMATION FOR SEQ ID NO:4:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Porcine ( i x ) FEATURE:
        ( A ) NAME/KEY: Region
        ( B ) LOCATION: 1..1260
        ( D ) OTHER INFORMATION: /note= "Genomic DNA encoding the B
        and part of the A2 domains of porcine factor
        VIII."

( x i ) SEQUENCE DESCRIPTION: SEQ ID NO:4:

```
GAATTCTTCA CTCAGATTCT CCTGTTCACA GTAGAAATTC AGTATTGTTA GCACTCTTTT      60
AGTTACCTGT ATCCTAAACC TAAGTCCTGC TCCCTTATAC TTACTCATCC TACAAATTGG     120
TCAGAGTATG TGTTTGGCAT TATGTTATGT GATTTGAATG CATTATCAGA TACTACTAGT     180
CTCATTTACA AATTAGAAAA CTGGAGCTCA GAGAGTTCCT TGGACTTGCT TAAAGCAACA     240
CAGCTGGTAA ATTGTATAGC TAGGATTCGA ACCGAGGCAA TCGTACTCTA GAACCCATGC     300
CACTATGTTG CATAGCATAA TAGCCCGCCT ATATAAACTT GGCTGAATTA AGTCACGATC     360
TATCATCACC AAAGAGTCCG TGTGACTAAG AGTCTCAACT ATTGTATGTC AATTATATTT     420
CTCCATTTTT ATCCCAATAT ATATTCATTT AAATCACAGC CCTTCTTGT  GGTCACAAAC     480
AGGTACACTA GAGCCATGGT TGGGCTGCAG TCCATGGTGT ACATTTAACC CAACGACCTC     540
GATATAATGG TACCGACTAG TGTTTTGTTT TTGTTTTTGT TTCATTTTTC TGGGAATAGA     600
AGAGAACCTC TAACACAGAT CTTGCTTGGG ACCTGGGCTG TGAGTAACCA GAGTTTTATT     660
CTTCCTTATC TCCAGGTCTC TGGGTCCTAG GGTGCCACAA CTCAGACTTG CGGAACAGAG     720
GGATGACAGC CTTACTGAAG GTGTATAGTT GTGACAGGGA CACTGGTGAT TATTATGACA     780
ACACTTATGA AGATATTCCA GGCTTCTTGC TGAGTGGAAA GAATGTCATT GAACCCAGAA     840
GCTTTGCCCA GAATTCAAGA CCCCCTAGTG CGAGCCAAAA GCAATTCCAA ACCATCACAA     900
GTCCAGAAGA TGACGTGGAG CTTGACCCGC AGTCTGGAGA GAGAACCCAA GCACTGGAAG     960
AACTAAGTGT CCCCTCTGGT GATGGGTCGA TGCTCTTGGG ACAGAATCCT GCTCCACATG    1020
GCTCATCCTC ATCTGATCTT CAAGAAGCCA GGAATGAGGC TGATGATTAT TTACCTGGAG    1080
CAAGAGAAAG AAACACGGCC CCATCCGCAG CGGCACGTCT CAGACCAGAG CTGCATCACA    1140
GTGCCGAAAG AGTACTTACT CCTGAGCCAG AGAAAGAGTT GAAGAAACTT GATTCTTAAA    1200
TGTCTAGTTC ATCAGACCTT CTAAAGACTT CGCCAACAAT TCCATCAGAC ACGTTGTCAG    1260
```

( 2 ) INFORMATION FOR SEQ ID NO:5:

( i ) SEQUENCE CHARACTERISTICS:
        ( A ) LENGTH: 1130 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
 ( A ) ORGANISM: Porcine
 ( F ) TISSUE TYPE: Blood ( i x ) FEATURE:
 ( A ) NAME/KEY: Region
 ( B ) LOCATION: 1..1130
 ( D ) OTHER INFORMATION: /note= "cDNA encoding A2 domain of porcine factor VIII."

( x i ) SEQUENCE DESCRIPTION: SEQ ID NO:5:

| | | | | | | |
|---|---|---|---|---|---|---|
| TAAGCACCCT | AAGACGTGGG | TGCACTACAT | CTCTGCAGAG | GAGGAGGACT | GGGACTACGC | 60 |
| CCCCGCGGTC | CCCAGCCCCA | GTGACAGAAG | TTATAAAAGT | CTCTACTTGA | ACAGTGGTCC | 120 |
| TCAGCGAATT | GGTAGGAAAT | ACAAAAAAGC | TCGATTCGTC | GCTTACACGG | ATGTAACATT | 180 |
| TAAGACTCGT | AAAGCTATTC | CGTATGAATC | AGGAATCCTG | GGACCTTTAC | TTTATGGAGA | 240 |
| AGTTGGAGAC | ACACTTTTGA | TTATATTTAA | GAATAAAGCG | AGCCGACCAT | ATAACATCTA | 300 |
| CCCTCATGGA | ATCACTGATG | TCAGCGCTTT | GCACCCAGGG | AGACTTCTAA | AAGGTTGGAA | 360 |
| ACATTTGAAA | GACATGCCAA | TTCTGCCAGG | AGAGACTTTC | AAGTATAAAT | GGACAGTGAC | 420 |
| TGTGGAAGAT | GGGCCAACCA | AGTCCGATCC | TCGGTGCCTG | ACCCGCTACT | ACTCGAGCTC | 480 |
| CATTAATCTA | GAGAAAGATC | TGGCTTCGGG | ACTCATTGGC | CCTCTCCTCA | TCTGCTACAA | 540 |
| AGAATCTGTA | GACCAAAGAG | AAACCAGAT | GATGTCAGAC | AAGAGAAACG | TCATCCTGTT | 600 |
| TTCTGTATTC | GATGAGAATC | AAAGCTGGTA | CCTCGCAGAG | AATATTCAGC | GCTTCCTCCC | 660 |
| CAATCCGGAT | GGATTACAGC | CCAGGATCC | AGAGTTCCAA | GCTTCTAACA | TCATGCACAG | 720 |
| CATCAATGGC | TATGTTTTTG | ATAGCTTGCA | GCTGTCGGTT | TGTTTGCACG | AGGTGGCATA | 780 |
| CTGGTACATT | CTAAGTGTTG | GAGCACAGAC | GGACTTCCTC | TCCGTCTTCT | TCTCTGGCTA | 840 |
| CACCTTCAAA | CACAAAATGG | TCTATGAAGA | CACACTCACC | CTGTTCCCCT | TCTCAGGAGA | 900 |
| AACGGTCTTC | ATGTCAATGG | AAAACCCAGG | TCTCTGGGTC | CTAGGGTGCC | ACAACTCAGA | 960 |
| CTTGCGGAAC | AGAGGGATGA | CAGCCTTACT | GAAGGTGTAT | AGTTGTGACA | GGGACATTGG | 1020 |
| TGATTATTAT | GACAACACTT | ATGAAGATAT | TCCAGGCTTC | TTGCTGAGTG | GAAAGAATGT | 1080 |
| CATTGAACCC | AGAAGCTTTG | CCCAGAATTC | AAGACCCCCT | AGTGCGAGCA | | 1130 |

( 2 ) INFORMATION FOR SEQ ID NO:6:

( i ) SEQUENCE CHARACTERISTICS:
  ( A ) LENGTH: 368 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
  ( A ) ORGANISM: Porcine
  ( F ) TISSUE TYPE: Spleen ( i x ) FEATURE:
  ( A ) NAME/KEY: Protein
  ( B ) LOCATION: 1..368
  ( D ) OTHER INFORMATION: /note= "Predicted amino acid sequence of the porcine factor VIII A2 domain,
defined as residues homologous to human factor
VIII amino acid sequence 373-740.

(Residues 1-4 are from known porcine amino acid sequence.)

(xi) SEQUENCE DESCRIPTION: SEQ ID NO:6:

Ser Val Ala Lys Lys His Pro Lys Thr Trp Val His Tyr Ile Ser Ala
1               5                   10                  15

Glu Glu Glu Asp Trp Asp Tyr Ala Pro Ala Val Pro Ser Pro Ser Asp
            20              25                  30

Arg Ser Tyr Lys Ser Leu Tyr Leu Asn Ser Gly Pro Gln Arg Ile Gly
        35              40              45

Arg Lys Tyr Lys Lys Ala Arg Phe Val Ala Tyr Thr Asp Val Thr Phe
    50              55                  60

Lys Thr Arg Lys Ala Ile Pro Tyr Glu Ser Gly Ile Leu Gly Pro Leu
65              70              75                      80

Leu Tyr Gly Glu Val Gly Asp Thr Leu Leu Ile Ile Phe Lys Asn Lys
                85                  90              95

Ala Ser Arg Pro Tyr Asn Ile Tyr Pro His Gly Ile Thr Asp Val Ser
            100             105             110

Ala Leu His Pro Gly Arg Leu Leu Lys Gly Trp Lys His Leu Lys Asp
        115             120             125

Met Pro Ile Leu Pro Gly Glu Thr Phe Lys Tyr Lys Trp Thr Val Thr
    130             135             140

Val Glu Asp Gly Pro Thr Lys Ser Asp Pro Arg Cys Leu Thr Arg Tyr
145             150             155                 160

Tyr Ser Ser Ser Ile Asn Leu Glu Lys Asp Leu Ala Ser Gly Leu Ile
                165             170             175

Gly Pro Leu Leu Ile Cys Tyr Lys Glu Ser Val Asp Gln Arg Gly Asn
            180             185             190

Gln Met Met Ser Asp Lys Arg Asn Val Ile Leu Phe Ser Val Phe Asp
        195             200             205

Glu Asn Gln Ser Trp Tyr Leu Ala Glu Asn Ile Gln Arg Phe Leu Pro
    210             215             220

Asn Pro Asp Gly Leu Gln Pro Gln Asp Pro Glu Phe Gln Ala Ser Asn
225             230             235             240

Ile Met His Ser Ile Asn Gly Tyr Val Phe Asp Ser Leu Gln Leu Ser
                245             250             255

Val Cys Leu His Glu Val Ala Tyr Trp Tyr Ile Leu Ser Val Gly Ala
            260             265             270

Gln Thr Asp Phe Leu Ser Val Phe Phe Ser Gly Tyr Thr Phe Lys His
        275             280             285

Lys Met Val Tyr Glu Asp Thr Leu Thr Leu Phe Pro Phe Ser Gly Glu
    290             295             300

Thr Val Phe Met Ser Met Glu Asn Pro Gly Leu Trp Val Leu Gly Cys
305             310             315             320

His Asn Ser Asp Leu Arg Asn Arg Gly Met Thr Ala Leu Leu Lys Val
                325             330             335

Tyr Ser Cys Asp Arg Asp Ile Gly Asp Tyr Tyr Asp Asn Thr Tyr Glu
            340             345             350

Asp Ile Pro Gly Phe Leu Leu Ser Gly Lys Asn Val Ile Glu Pro Arg
        355             360             365

(2) INFORMATION FOR SEQ ID NO:7:

(i) SEQUENCE CHARACTERISTICS:

(A) LENGTH: 7493 base pairs
(B) TYPE: nucleic acid
(C) STRANDEDNESS: single
(D) TOPOLOGY: linear (i i) MOLECULE TYPE: cDNA to mRNA (i i i) HYPOTHETICAL: NO (i v) ANTI-SENSE: NO (v i) ORIGINAL SOURCE:
 (A) ORGANISM: Mus musculus (i x) FEATURE:
 (A) NAME/KEY: repeat_unit
 (B) LOCATION: 1..407
 (D) OTHER INFORMATION: /rpt_type="terminal"
  / note="5'UTR"

(i x) FEATURE:
 (A) NAME/KEY: misc_feature
 (B) LOCATION: 7471..7476
 (D) OTHER INFORMATION: /function="PolyA_signal"

(i x) FEATURE:
 (A) NAME/KEY: repeat_unit
 (B) LOCATION: 7368..7493
 (D) OTHER INFORMATION: /rpt_type="terminal"
  / note="3'UTR"

(i x) FEATURE:
 (A) NAME/KEY: misc_feature
 (B) LOCATION: 408..7367
 (D) OTHER INFORMATION: /product="Coagulation Factor VIII"

(x) PUBLICATION INFORMATION:
 (A) AUTHORS: Elder, F.
  Lakich, D.
  Gitschier, J.
 (B) TITLE: Sequence of the Murine Factor VIII cDNA.
 (C) JOURNAL: Genomics
 (D) VOLUME: 16
 (F) PAGES: 374-379
 (G) DATE: 1993
 (K) RELEVANT RESIDUES IN SEQ ID NO:7: FROM 1 TO 7476

(x i) SEQUENCE DESCRIPTION: SEQ ID NO:7:

```
TCTAGAGTTT CTTTGCTACA GGTACCAAGG AACAGTCTTT TAGAATAGGC TAGGAATTTA      60
AATACACCTG AACGCCCCTC CTCAGTATTC TGTTCCTTTT CTTAAGGATT CAAACTTGTT     120
AGGATGCACC CAGCAGGAAA TGGGTTAAGC CTTAGCTCAG CCACTCTTCC TATTCCAGTT     180
TTCCTGTGCC TGCTTCCTAC TACCCAAAAG GAAGTAATCC TTCAGATCTG TTTTGTGCTA     240
ATGCTACTTT CACTCACAGT AGATAAACTT CCAGAAAATC CTCTGCAAAA TATTTAGGAC     300
TTTTTACTAA ATCATTACAT TTCTTTTGT TCTTAAAAGC TAAAGTTATT TTAGAGAAGA     360
GTTAAATTTT CATTTCTTTA GTTGAACATT TTCTAGTAAT AAAAGCCATG CAAATAGCAC     420
TCTTCGCTTG CTTCTTTCTG AGCCTTTTCA ATTTCTGCTC TAGTGCCATC AGAAGATACT     480
ACCTTGGTGC AGTGGAATTG TCCTGGAACT ATATTCAGAG TGATCTGCTC AGTGTGCTGC     540
ATACAGACTC AAGATTTCTT CCTAGAATGT CAACATCTTT TCCATTCAAC ACCTCCATCA     600
TGTATAAAAA GACTGTGTTT GTAGAGTACA AGGACCAGCT TTTCAACATT GCCAAGCCCA     660
GGCCACCCTG GATGGGTTTG CTAGGTCCTA CCATTTGGAC TGAGGTTCAT GACACAGTGG     720
TCATTACACT TAAAAACATG GCTTCTCATC CTGTCAGTCT TCATGCTGTT GGTGTGTCCT     780
ACTGGAAAGC TTCTGAGGGA GATGAATATG AAGATCAGAC AAGCCAAATG GAGAAGGAAG     840
ATGATAAAGT TTTCCCTGGT GAAAGTCATA CTTATGTTTG GCAAGTCCTG AAAGAGAATG     900
GTCCAATGGC CTCTGACCCT CCATGTCTCA CTTACTCATA TATGTCTCAT GTGGATCTGG     960
```

```
TGAAAGATTT  GAATTCAGGC  CTCATTGGAG  CTCTGCTAGT  ATGTAAAGAA  GGCAGTCTCT   1020

CCAAAGAAAG  AACACAGATG  TTGTACCAAT  TTGTACTGCT  TTTTGCTGTA  TTTGATGAAG   1080

GGAAGAGCTG  GCACTCAGAA  ACAAACGACT  CTTATACACA  GTCTATGGAT  TCTGCATCTG   1140

CTAGAGACTG  GCCTAAAATG  CACACAGTCA  ATGGCTATGT  AAACAGGTCT  CTTCCAGGTC   1200

TGATTGGATG  CCATAGGAAA  TCAGTCTACT  GGCACGTGAT  TGGAATGGGC  ACCACTCCTG   1260

AAATACACTC  AATATTCCTC  GAAGGTCACA  CATTTTTGT   GAGGAACCAC  CGTCAAGCTT   1320

CATTGGAGAT  ATCACCAATA  ACTTTCCTTA  CTGCTCAAAC  ACTCTTGATA  GATCTTGGGC   1380

AGTTCCTACT  ATTTTGTCAT  ATCTCTTCCC  ATAAACATGA  TGGCATGGAA  GCTTATGTCA   1440

AAGTAGATAG  CTGCCCTGAG  GAATCCCAAT  GGCAAAAGAA  AAATAATAAT  GAGGAAATGG   1500

AAGATTATGA  TGATGATCTT  TATTCAGAAA  TGGATATGTT  CACATTGGAT  TATGACAGCT   1560

CTCCTTTTAT  CCAAATTCGC  TCGGTTGCTA  AAAAGTACCC  TAAAACTTGG  ATACATTATA   1620

TTTCTGCTGA  GGAGGAAGAC  TGGGACTATG  CACCTTCAGT  TCCTACCTCG  GATAATGGAA   1680

GTTATAAAAG  CCAGTATCTG  AGCAATGGTC  CTCATCGGAT  TGGTAGGAAA  TATAAAAAG    1740

TCAGATTTAT  AGCATACACA  GATGAAACCT  TTAAGACTCG  TGAAACTATT  CAGCATGAAT   1800

CAGGACTCTT  GGGACCTTTA  CTTTATGGAG  AAGTTGGAGA  CACACTGTTG  ATTATTTTA    1860

AGAATCAAGC  AAGCCGACCA  TATAACATTT  ACCCTCATGG  AATCACTGAT  GTCAGTCCTC   1920

TACATGCAAG  GAGATTGCCA  AGAGGTATAA  AGCACGTGAA  GGATTTGCCA  ATTCATCCAG   1980

GAGAGATATT  CAAGTACAAG  TGGACAGTTA  CAGTAGAAGA  TGGACCAACT  AAATCAGATC   2040

CACGGTGCCT  GACCCGCTAT  TATTCAAGTT  TCATTAACCC  TGAGAGAGAT  CTAGCTTCAG   2100

GACTGATTGG  CCCTCTTCTC  ATCTGCTACA  AGAATCTGT   AGATCAAAGG  GGAAACCAGA   2160

TGATGTCAGA  CAAAAGAAAT  GTCATCCTGT  TTTCTATATT  TGATGAGAAC  CAAAGCTGGT   2220

ACATCACAGA  GAACATGCAA  CGCTTCCTCC  CCAATGCAGC  TAAAACACAG  CCCCAGGACC   2280

CTGGGTTCCA  GGCCTCCAAC  ATCATGCACA  GCATCAATGG  CTATGTTTTT  GATAGCTTGG   2340

AGTTGACAGT  TTGTTTGCAT  GAGGTGGCAT  ACTGGCACAT  TCTCAGTGTT  GGAGCACAGA   2400

CAGACTTCTT  ATCTATCTTC  TTCTCTGGAT  ATACTTTCAA  ACACAAAATG  GTCTATGAAG   2460

ATACACTTAC  CCTGTTCCCA  TTCTCAGGAG  AAACTGTCTT  TATGTCGATG  GAAAACCCAG   2520

GTCTATGGGT  CTTGGGGTGT  CATAATTCAG  ACTTTCGGAA  GAGAGGTATG  ACAGCATTGC   2580

TGAAAGTTTC  TAGTTGTGAC  AAGAGCACTA  GTGATTATTA  TGAAGAAATA  TATGAAGATA   2640

TTCCAACACA  GTTGGTGAAT  GAGAACAATG  TCATTGATCC  CAGAAGCTTC  TTCCAGAATA   2700

CAAATCATCC  TAATACTAGG  AAAAAGAAAT  TCAAAGATTC  CACAATTCCA  AAAAATGATA   2760

TGGAGAAGAT  TGAGCCTCAG  TTTGAAGAGA  TAGCAGAGAT  GCTTAAAGTA  CAGAGTGTCT   2820

CAGTTAGTGA  CATGTTGATG  CTCTTGGGAC  AGAGTCATCC  TACTCCACAT  GGCTTATTTT   2880

TATCAGATGG  CCAAGAAGCC  ATCTATGAGG  CTATTCATGA  TGATCATTCA  CCAAATGCAA   2940

TAGACAGCAA  TGAAGGCCCA  TCTAAAGTGA  CCCAACTCAG  GCCAGAATCC  CATCACAGTG   3000

AGAAAATAGT  ATTTACTCCT  CAGCCCGGCC  TCCAGTTAAG  ATCCAATAAA  AGTTTGGAGA   3060

CAACTATAGA  AGTAAAGTGG  AAGAAACTTG  GTTTGCAAGT  TTCTAGTTTG  CCAAGTAATC   3120

TAATGACTAC  AACAATTCTG  TCAGACAATT  TGAAAGCAAC  TTTTGAAAAG  ACAGATTCTT   3180

CAGGATTTCC  AGATATGCCA  GTTCACTCTA  GTAGTAAATT  AAGTACTACT  GCATTTGGTA   3240

AGAAAGCATA  TTCCCTTGTT  GGGTCTCATG  TACCTTTAAA  CGCGAGTGAA  GAAAATAGTG   3300

ATTCCAACAT  ATTGGATTCA  ACTTTAATGT  ATAGTCAAGA  AAGTTTACCA  AGAGATAATA   3360
```

```
TATTATCAAT AGAGAATGAT AGATTACTCA GAGAGAAGAG GTTTCATGGA ATTGCTTTAT    3420
TGACCAAAGA TAATACTTTA TTCAAAGACA ATGTCTCCTT AATGAAAACA AACAAAACAT    3480
ATAATCATTC AACAACTAAT GAAAAACTAC ACACTGAGAG CCCAACATCA ATTGAGAATA    3540
GTACAACAGA CTTGCAAGAT GCCATATTAA AGGTCAATAG TGAGATTCAA GAAGTAACAG    3600
CTTTGATTCA TGATGGAACA CTTTTAGGCA AAAATTCTAC ATATTTGAGA CTAAACCATA    3660
TGCTAAATAG AACTACCTCA ACAAAAAATA AGACATATT TCATAGAAAA GATGAAGATC     3720
CTATTCCACA AGATGAAGAG AATACAATCA TGCCATTTTC CAAGATGTTG TTCTTGTCAG    3780
AATCTTCAAA TTGGTTTAAA AAGACCAATG GAAATAATTC CTTGAACTCT GAGCAAGAAC    3840
ATAGTCCAAA GCAATTAGTA TATTTAATGT TTAAAAAATA TGTAAAAAAT CAAAGTTTCT    3900
TGTCAGAGAA AAATAAAGTC ACAGTAGAAC AGGATGGATT TACAAAGAAC ATAGGACTTA    3960
AAGACATGGC TTTTCCACAT AATATGAGCA TATTTCTTAC CACTTTGTCT AACGTACATG    4020
AAAATGGTAG GCACAATCAA GAAAAAAATA TTCAGGAAGA GATAGAGAAG GAAGCACTAA    4080
TTGAAGAGAA AGTAGTTTTG CCCCAGGTGC ACGAAGCAAC TGGCTCTAAG AATTTCTTGA    4140
AGACATATT GATACTAGGC ACTAGGCAAA ATATAAGTTT ATATGAAGTA CATGTACCAG     4200
TACTTCAAAA CATCACATCA ATAAACAATT CAACAAATAC AGTACAGATT CACATGGAGC    4260
ATTTCTTTAA AGAAGGAAG GACAAGGAAA CAAATTCAGA AGGCTTGGTA AATAAAACCA     4320
GAGAAATGGT AAAAAACTAT CCAAGCCAGA AGAATATTAC TACTCAACGT AGTAAACGGG    4380
CTTTGGGACA ATTCAGACTG TCAACTCAAT GGCTTAAAAC CATAAACTGT TCAACACAGT    4440
GTATCATTAA ACAGATAGAC CACAGCAAGG AAATGAAAAA GTTCATTACT AAATCTTCCT    4500
TATCAGATTC TTCTGTGATT AAAAGCACCA CTCAGACAAA TAGTTCTGAC TCACACATTG    4560
TAAAAACATC AGCATTTCCA CCAATAGATC TCAAAGGAG TCCATTCCAA AACAAATTTT     4620
CTCATGTTCA AGCATCATCC TACATTTATG ACTTTAAGAC AAAAAGTTCA AGAATTCAAG    4680
AAAGCAATAA TTTCTTAAAA GAAACCAAAA TAAATAACCC TTCTTTAGCC ATTCTACCAT    4740
GGAATATGTT CATAGATCAA GGAAAATTTA CCTCCCCAGG GAAAAGTAAC ACAAACTCAG    4800
TCACATATAA GAAACGTGAG AACATTATTT TCTTGAAACC AACTTTGCCT GAAGAATCTG    4860
GCAAAATTGA ATTGCTTCCT CAAGTTTCCA TTCAAGAGGA AGAAATTTTA CCTACAGAAA    4920
CTAGCCATGG ATCTCCTGGA CACTTGAATC TCATGAAAGA GGTCTTTCTT CAGAAAATAC    4980
AGGGGCCTAC TAAATGGAAT AAAGCAAAGA GGCATGGAGA AGTATAAAA GGTAAAACAG     5040
AGAGCTCTAA AAATACTCGC TCAAAACTGC TAAATCATCA TGCTTGGGAT TATCATTATG    5100
CTGCACAGAT ACCAAAAGAT ATGTGGAAAT CCAAAGAGAA GTCACCAGAA ATTATATCCA    5160
TTAAGCAAGA GGACACCATT TTGTCTCTGA GGCCTCATGG AAACAGTCAT TCAATAGGGG    5220
CAAATGAGAA ACAAAATTGG CCTCAAAGAG AAACCACTTG GGTAAAGCAA GGCCAAACTC    5280
AAAGGACATG CTCTCAAATC CCACCAGTGT TGAAACGACA TCAAAGGGAA CTTAGTGCTT    5340
TTCAATCAGA ACAAGAAGCA ACTGACTATG ATGATGCCAT CACCATTGAA ACAATCGAGG    5400
ATTTTGACAT TTACAGTGAG GACATAAAGC AAGGTCCCCG CAGCTTTCAA CAGAAAACAA    5460
GGCACTATTT TATTGCAGCT GTGGAACGAC TCTGGGACTA TGGGATGAGT ACATCTCATG    5520
TTCTACGAAA TAGGTATCAA AGTGACAATG TACCTCAGTT CAAGAAAGTA GTTTTCCAGG    5580
AATTTACTGA TGGCTCCTTT AGTCAGCCCT TATATCGTGG AGAATTAAAT GAACACCTGG    5640
GGTTGTTGGG CCCATATATA AGAGCAGAAG TTGAAGACAA CATTATGGTA ACTTTCAAAA    5700
ACCAGGCCTC CCGTCCCTAC TCCTTCTATT CTAGCCTCAT TTCTTATAAA GAAGATCAGA    5760
```

-continued

| | | | | | |
|---|---|---|---|---|---|
| GAGGAGAAGA | ACCTAGAAGA | AACTTTGTCA | AGCCTAATGA | AACCAAAATT | TATTTTTGGA | 5820 |
| AAGTACAACA | TCATATGGCA | CCCACAGAAG | ATGAGTTTGA | CTGCAAGGCC | TGGGCTTATT | 5880 |
| TCTCTGATGT | TGATCTTGAA | AGAGATATGC | ACTCGGGATT | AATTGGACCC | CTTCTGATTT | 5940 |
| GCCACGCGAA | CACACTGAAT | CCTGCTCATG | GGAGACAAGT | GTCAGTACAG | GAATTTGCTC | 6000 |
| TGCTTTTCAC | TATCTTTGAT | GAGACCAAGA | GCTGGTACTT | CACTGAAAAC | GTGAAAGGA | 6060 |
| ACTGCAAGAC | ACCCTGCAAT | TTCCAGATGG | AAGACCCCAC | TTTGAAAGAG | AATTATCGCT | 6120 |
| TCCATGCAAT | CAATGGTTAT | GTAATGGATA | CCCTACCAGG | CTTAGTAATG | GCTCAAGATC | 6180 |
| AAAGGATTCG | ATGGTATCTT | CTCAGCATGG | GCAACAATGA | GAACATCCAA | TCTATTCATT | 6240 |
| TCAGTGGACA | TGTTTTCACT | GTACGGAAAA | AAGAGGAGTA | TAAAATGGCA | GTGTACAACC | 6300 |
| TCTACCCAGG | TGTTTTTGAG | ACTCTGGAAA | TGATACCATC | CAGAGCTGGA | ATATGGCGAG | 6360 |
| TAGAATGCCT | TATTGGCGAG | CACTTACAGG | CTGGGATGAG | CACTCTTTTT | CTGGTGTACA | 6420 |
| GCAAGCAGTG | TCAGATTCCT | CTTGGAATGG | CTTCTGAAG | CATCCGTGAT | TTCCAGATTA | 6480 |
| CAGCTTCAGG | ACATTATGGA | CAGTGGGCCC | CAAACCTGGC | AAGACTTCAT | TATTCCGGAT | 6540 |
| CAATCAATGC | CTGGAGTACC | AAGGAGCCCT | TTTCTTGGAT | CAAGGTAGAT | CTGTTGGCAC | 6600 |
| CAATGATTGT | TCATGGCATC | AAGACTCAGG | GTGCTCGTCA | GAAATTTTCC | AGCCTTTATA | 6660 |
| TCTCTCAATT | TATCATCATG | TATAGCCTGG | ATGGGAAGAA | GTGGCTGAGT | TATCAAGGAA | 6720 |
| ATTCCACTGG | AACCTTAATG | GTTTTCTTTG | GCAATGTGGA | CTCATCTGGG | ATTAAGCATA | 6780 |
| ATAGTTTTAA | TCCTCCAATT | ATTGCTCGAT | ATATCCGTTT | GCACCCCACT | CATTCTAGCA | 6840 |
| TCCGTAGTAC | TCTTCGCATG | GAGTTGATGG | GCTGTGATTT | AAACAGTTGC | AGCATACCAT | 6900 |
| TGGGAATGGA | AAGTAAAGTA | ATATCAGATA | CACAAATCAC | TGCCTCATCC | TACTTCACCA | 6960 |
| ACATGTTTGC | TACTTGGTCT | CCTTCACAAG | CTCGACTTCA | CCTCCAGGGA | AGGACTAATG | 7020 |
| CCTGGCGACC | TCAGGTGAAT | GATCCAAAAC | AATGGTTGCA | AGTGGACTTA | CAAAAGACAA | 7080 |
| TGAAAGTCAC | TGGAATAATA | ACCCAGGGAG | TGAAATCTCT | CTTTACCAGC | ATGTTTGTGA | 7140 |
| AAGAGTTCCT | TATTTCCAGC | AGTCAAGATG | GCCATCACTG | GACTCAAATT | TTATACAATG | 7200 |
| GCAAGGTAAA | GGTTTTTCAG | GGGAATCAGG | ACTCATCCAC | ACCTATGATG | AATTCTCTAG | 7260 |
| ACCCACCATT | ACTCACTCGC | TATCTTCGAA | TTCACCCCCA | GATCTGGGAG | CACCAAATTG | 7320 |
| CTCTGAGGCT | TGAGATTCTA | GGATGTGAGG | CCCAGCAGCA | ATACTGAGGT | AGCCTCTGCA | 7380 |
| TCACCTGCTT | ATTCCCCTTC | CTCAGCTCAA | AGATTGTCTT | AATGTTTTAT | TGCTGTGAAG | 7440 |
| AGACACTATG | ACCATGGCAA | CTCTTTATAA | AATAAAGCAT | TTAATCAGGG | CTT | 7493 |

( 2 ) INFORMATION FOR SEQ ID NO:8:

( i ) SEQUENCE CHARACTERISTICS:
        ( A ) LENGTH: 2319 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Mus musculus ( x ) PUBLICATION INFORMATION:

(A) AUTHORS: Elder, F.
    Lakich, D.
    Gitschier, J.
(B) TITLE: Sequence of the Murine Factor VIII cDNA.
(C) JOURNAL: Genomics
(D) VOLUME: 16
(F) PAGES: 374-379
(G) DATE: 1993
(K) RELEVANT RESIDUES IN SEQ ID NO:8: FROM 1 TO 2319

(xi) SEQUENCE DESCRIPTION: SEQ ID NO:8:

```
Met Gln Ile Ala Leu Phe Ala Cys Phe Phe Leu Ser Leu Phe Asn Phe
1               5                   10                  15

Cys Ser Ser Ala Ile Arg Arg Tyr Tyr Leu Gly Ala Val Glu Leu Ser
            20                  25                  30

Trp Asn Tyr Ile Gln Ser Asp Leu Leu Ser Val Leu His Thr Asp Ser
                35                  40                  45

Arg Phe Leu Pro Arg Met Ser Ser Phe Pro Phe Asn Thr Ser Ile
    50                  55                  60

Met Tyr Lys Lys Thr Val Phe Val Glu Tyr Lys Asp Gln Leu Phe Asn
65                  70                  75                  80

Ile Ala Lys Pro Arg Pro Pro Trp Met Gly Leu Leu Gly Pro Thr Ile
                    85                  90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Asp Glu Tyr Glu Asp Gln Thr Ser Gln Met Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Met Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
        195                 200                 205

Thr Gln Met Leu Tyr Gln Phe Val Leu Leu Phe Ala Val Phe Asp Glu
    210                 215                 220

Gly Lys Ser Trp His Ser Glu Thr Asn Asp Ser Tyr Thr Gln Ser Met
225                 230                 235                 240

Asp Ser Ala Ser Ala Arg Asp Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Ile His Ser
        275                 280                 285

Ile Phe Leu Glu Gly His Thr Phe Phe Val Arg Asn His Arg Gln Ala
    290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
            340                 345                 350

Ser Gln Trp Gln Lys Lys Asn Asn Asn Glu Glu Met Glu Asp Tyr Asp
        355                 360                 365
```

```
Asp Asp Leu Tyr Ser Glu Met Asp Met Phe Thr Leu Asp Tyr Asp Ser
    370             375             380

Ser Pro Phe Ile Gln Ile Arg Ser Val Ala Lys Lys Tyr Pro Lys Thr
385             390             395                         400

Trp Ile His Tyr Ile Ser Ala Glu Glu Asp Trp Asp Tyr Ala Pro
                405             410             415

Ser Val Pro Thr Ser Asp Asn Gly Ser Tyr Lys Ser Gln Tyr Leu Ser
            420             425             430

Asn Gly Pro His Arg Ile Gly Arg Lys Tyr Lys Lys Val Arg Phe Ile
        435             440             445

Ala Tyr Thr Asp Glu Thr Phe Lys Thr Arg Glu Thr Ile Gln His Glu
450             455             460

Ser Gly Leu Leu Gly Pro Leu Leu Tyr Gly Glu Val Gly Asp Thr Leu
465             470             475             480

Leu Ile Ile Phe Lys Asn Gln Ala Ser Arg Pro Tyr Asn Ile Tyr Pro
                485             490             495

His Gly Ile Thr Asp Val Ser Pro Leu His Ala Arg Arg Leu Pro Arg
            500             505             510

Gly Ile Lys His Val Lys Asp Leu Pro Ile His Pro Gly Glu Ile Phe
        515             520             525

Lys Tyr Lys Trp Thr Val Thr Val Glu Asp Gly Pro Thr Lys Ser Asp
    530             535             540

Pro Arg Cys Leu Thr Arg Tyr Tyr Ser Ser Phe Ile Asn Pro Glu Arg
545             550             555             560

Asp Leu Ala Ser Gly Leu Ile Gly Pro Leu Leu Ile Cys Tyr Lys Glu
            565             570             575

Ser Val Asp Gln Arg Gly Asn Gln Met Met Ser Asp Lys Arg Asn Val
        580             585             590

Ile Leu Phe Ser Ile Phe Asp Glu Asn Gln Ser Trp Tyr Ile Thr Glu
        595             600             605

Asn Met Gln Arg Phe Leu Pro Asn Ala Ala Lys Thr Gln Pro Gln Asp
    610             615             620

Pro Gly Phe Gln Ala Ser Asn Ile Met His Ser Ile Asn Gly Tyr Val
625             630             635             640

Phe Asp Ser Leu Glu Leu Thr Val Cys Leu His Glu Val Ala Tyr Trp
                645             650             655

His Ile Leu Ser Val Gly Ala Gln Thr Asp Phe Leu Ser Ile Phe Phe
            660             665             670

Ser Gly Tyr Thr Phe Lys His Lys Met Val Tyr Glu Asp Thr Leu Thr
        675             680             685

Leu Phe Pro Phe Ser Gly Glu Thr Val Phe Met Ser Met Glu Asn Pro
    690             695             700

Gly Leu Trp Val Leu Gly Cys His Asn Ser Asp Phe Arg Lys Arg Gly
705             710             715             720

Met Thr Ala Leu Leu Lys Val Ser Ser Cys Asp Lys Ser Thr Ser Asp
                725             730             735

Tyr Tyr Glu Glu Ile Tyr Glu Asp Ile Pro Thr Gln Leu Val Asn Glu
            740             745             750

Asn Asn Val Ile Asp Pro Arg Ser Phe Phe Gln Asn Thr Asn His Pro
        755             760             765

Asn Thr Arg Lys Lys Lys Phe Lys Asp Ser Thr Ile Pro Lys Asn Asp
770             775             780

Met Glu Lys Ile Glu Pro Gln Phe Glu Glu Ile Ala Glu Met Leu Lys
```

-continued

| 785 | | | | | 790 | | | | | 795 | | | | | 800 |
|---|---|---|---|---|---|---|---|---|---|---|---|---|---|---|---|
| Val | Gln | Ser | Val | Ser | Val | Ser | Asp | Met | Leu | Met | Leu | Leu | Gly | Gln | Ser |
| | | | | 805 | | | | | 810 | | | | | 815 | |
| His | Pro | Thr | Pro | His | Gly | Leu | Phe | Leu | Ser | Asp | Gly | Gln | Glu | Ala | Ile |
| | | | 820 | | | | | 825 | | | | | 830 | | |
| Tyr | Glu | Ala | Ile | His | Asp | Asp | His | Ser | Pro | Asn | Ala | Ile | Asp | Ser | Asn |
| | | | 835 | | | | | 840 | | | | | 845 | | |
| Glu | Gly | Pro | Ser | Lys | Val | Thr | Gln | Leu | Arg | Pro | Glu | Ser | His | His | Ser |
| | 850 | | | | | 855 | | | | | 860 | | | | |
| Glu | Lys | Ile | Val | Phe | Thr | Pro | Gln | Pro | Gly | Leu | Gln | Leu | Arg | Ser | Asn |
| 865 | | | | | 870 | | | | | 875 | | | | | 880 |
| Lys | Ser | Leu | Glu | Thr | Thr | Ile | Glu | Val | Lys | Trp | Lys | Lys | Leu | Gly | Leu |
| | | | | 885 | | | | | 890 | | | | | 895 | |
| Gln | Val | Ser | Ser | Leu | Pro | Ser | Asn | Leu | Met | Thr | Thr | Thr | Ile | Leu | Ser |
| | | | | 900 | | | | | 905 | | | | | 910 | |
| Asp | Asn | Leu | Lys | Ala | Thr | Phe | Glu | Lys | Thr | Asp | Ser | Ser | Gly | Phe | Pro |
| | | | 915 | | | | | 920 | | | | | 925 | | |
| Asp | Met | Pro | Val | His | Ser | Ser | Ser | Lys | Leu | Ser | Thr | Thr | Ala | Phe | Gly |
| | | 930 | | | | | 935 | | | | | 940 | | | |
| Lys | Lys | Ala | Tyr | Ser | Leu | Val | Gly | Ser | His | Val | Pro | Leu | Asn | Ala | Ser |
| 945 | | | | | 950 | | | | | 955 | | | | | 960 |
| Glu | Glu | Asn | Ser | Asp | Ser | Asn | Ile | Leu | Asp | Ser | Thr | Leu | Met | Tyr | Ser |
| | | | | 965 | | | | | 970 | | | | | 975 | |
| Gln | Glu | Ser | Leu | Pro | Arg | Asp | Asn | Ile | Leu | Ser | Ile | Glu | Asn | Asp | Arg |
| | | | 980 | | | | | 985 | | | | | 990 | | |
| Leu | Leu | Arg | Glu | Lys | Arg | Phe | His | Gly | Ile | Ala | Leu | Leu | Thr | Lys | Asp |
| | | 995 | | | | | 1000 | | | | | 1005 | | | |
| Asn | Thr | Leu | Phe | Lys | Asp | Asn | Val | Ser | Leu | Met | Lys | Thr | Asn | Lys | Thr |
| | | 1010 | | | | | 1015 | | | | | 1020 | | | |
| Tyr | Asn | His | Ser | Thr | Thr | Asn | Glu | Lys | Leu | His | Thr | Glu | Ser | Pro | Thr |
| 1025 | | | | | 1030 | | | | | 1035 | | | | | 1040 |
| Ser | Ile | Glu | Asn | Ser | Thr | Thr | Asp | Leu | Gln | Asp | Ala | Ile | Leu | Lys | Val |
| | | | | 1045 | | | | | 1050 | | | | | 1055 | |
| Asn | Ser | Glu | Ile | Gln | Glu | Val | Thr | Ala | Leu | Ile | His | Asp | Gly | Thr | Leu |
| | | | | 1060 | | | | | 1065 | | | | | 1070 | |
| Leu | Gly | Lys | Asn | Ser | Thr | Tyr | Leu | Arg | Leu | Asn | His | Met | Leu | Asn | Arg |
| | | | 1075 | | | | | 1080 | | | | | 1085 | | |
| Thr | Thr | Ser | Thr | Lys | Asn | Lys | Asp | Ile | Phe | His | Arg | Lys | Asp | Glu | Asp |
| | | | 1090 | | | | | 1095 | | | | | 1100 | | |
| Pro | Ile | Pro | Gln | Asp | Glu | Glu | Asn | Thr | Ile | Met | Pro | Phe | Ser | Lys | Met |
| 1105 | | | | | 1110 | | | | | 1115 | | | | | 1120 |
| Leu | Phe | Leu | Ser | Glu | Ser | Ser | Asn | Trp | Phe | Lys | Lys | Thr | Asn | Gly | Asn |
| | | | | 1125 | | | | | 1130 | | | | | 1135 | |
| Asn | Ser | Leu | Asn | Ser | Glu | Gln | Glu | His | Ser | Pro | Lys | Gln | Leu | Val | Tyr |
| | | | 1140 | | | | | 1145 | | | | | 1150 | | |
| Leu | Met | Phe | Lys | Lys | Tyr | Val | Lys | Asn | Gln | Ser | Phe | Leu | Ser | Glu | Lys |
| | | 1155 | | | | | 1160 | | | | | 1165 | | | |
| Asn | Lys | Val | Thr | Val | Glu | Gln | Asp | Gly | Phe | Thr | Lys | Asn | Ile | Gly | Leu |
| | 1170 | | | | | 1175 | | | | | 1180 | | | | |
| Lys | Asp | Met | Ala | Phe | Pro | His | Asn | Met | Ser | Ile | Phe | Leu | Thr | Thr | Leu |
| 1185 | | | | | 1190 | | | | | 1195 | | | | | 1200 |
| Ser | Asn | Val | His | Glu | Asn | Gly | Arg | His | Asn | Gln | Glu | Lys | Asn | Ile | Gln |
| | | | | 1205 | | | | | 1210 | | | | | 1215 | |

```
Glu Glu Ile Glu Lys Glu Ala Leu Ile Glu Glu Lys Val Val Leu Pro
        1220            1225            1230

Gln Val His Glu Ala Thr Gly Ser Lys Asn Phe Leu Lys Asp Ile Leu
        1235            1240            1245

Ile Leu Gly Thr Arg Gln Asn Ile Ser Leu Tyr Glu Val His Val Pro
        1250            1255            1260

Val Leu Gln Asn Ile Thr Ser Ile Asn Asn Ser Thr Asn Thr Val Gln
1265            1270            1275            1280

Ile His Met Glu His Phe Phe Lys Arg Arg Lys Asp Lys Glu Thr Asn
            1285            1290            1295

Ser Glu Gly Leu Val Asn Lys Thr Arg Glu Met Val Lys Asn Tyr Pro
            1300            1305            1310

Ser Gln Lys Asn Ile Thr Thr Gln Arg Ser Lys Arg Ala Leu Gly Gln
        1315            1320            1325

Phe Arg Leu Ser Thr Gln Trp Leu Lys Thr Ile Asn Cys Ser Thr Gln
        1330            1335            1340

Cys Ile Ile Lys Gln Ile Asp His Ser Lys Glu Met Lys Lys Phe Ile
1345            1350            1355            1360

Thr Lys Ser Ser Leu Ser Asp Ser Ser Val Ile Lys Ser Thr Thr Gln
                1365            1370            1375

Thr Asn Ser Ser Asp Ser His Ile Val Lys Thr Ser Ala Phe Pro Pro
            1380            1385            1390

Ile Asp Leu Lys Arg Ser Pro Phe Gln Asn Lys Phe Ser His Val Gln
            1395            1400            1405

Ala Ser Ser Tyr Ile Tyr Asp Phe Lys Thr Lys Ser Ser Arg Ile Gln
        1410            1415            1420

Glu Ser Asn Asn Phe Leu Lys Glu Thr Lys Ile Asn Asn Pro Ser Leu
1425            1430            1435            1440

Ala Ile Leu Pro Trp Asn Met Phe Ile Asp Gln Gly Lys Phe Thr Ser
                1445            1450            1455

Pro Gly Lys Ser Asn Thr Asn Ser Val Thr Tyr Lys Lys Arg Glu Asn
            1460            1465            1470

Ile Ile Phe Leu Lys Pro Thr Leu Pro Glu Glu Ser Gly Lys Ile Glu
            1475            1480            1485

Leu Leu Pro Gln Val Ser Ile Gln Glu Glu Glu Ile Leu Pro Thr Glu
        1490            1495            1500

Thr Ser His Gly Ser Pro Gly His Leu Asn Leu Met Lys Glu Val Phe
1505            1510            1515            1520

Leu Gln Lys Ile Gln Gly Pro Thr Lys Trp Asn Lys Ala Lys Arg His
            1525            1530            1535

Gly Glu Ser Ile Lys Gly Lys Thr Glu Ser Ser Lys Asn Thr Arg Ser
            1540            1545            1550

Lys Leu Leu Asn His His Ala Trp Asp Tyr His Tyr Ala Ala Gln Ile
        1555            1560            1565

Pro Lys Asp Met Trp Lys Ser Lys Glu Lys Ser Pro Glu Ile Ile Ser
        1570            1575            1580

Ile Lys Gln Glu Asp Thr Ile Leu Ser Leu Arg Pro His Gly Asn Ser
1585            1590            1595            1600

His Ser Ile Gly Ala Asn Glu Lys Gln Asn Trp Pro Gln Arg Glu Thr
            1605            1610            1615

Thr Trp Val Lys Gln Gly Gln Thr Gln Arg Thr Cys Ser Gln Ile Pro
            1620            1625            1630

Pro Val Leu Lys Arg His Gln Arg Glu Leu Ser Ala Phe Gln Ser Glu
        1635            1640            1645
```

Gln Glu Ala Thr Asp Tyr Asp Asp Ala Ile Thr Ile Glu Thr Ile Glu
              1650                1655                1660

Asp Phe Asp Ile Tyr Ser Glu Asp Ile Lys Gln Gly Pro Arg Ser Phe
1665                1670                1675                1680

Gln Gln Lys Thr Arg His Tyr Phe Ile Ala Ala Val Glu Arg Leu Trp
              1685                1690                1695

Asp Tyr Gly Met Ser Thr Ser His Val Leu Arg Asn Arg Tyr Gln Ser
              1700                1705                1710

Asp Asn Val Pro Gln Phe Lys Lys Val Val Phe Gln Glu Phe Thr Asp
              1715                1720                1725

Gly Ser Phe Ser Gln Pro Leu Tyr Arg Gly Glu Leu Asn Glu His Leu
              1730                1735                1740

Gly Leu Leu Gly Pro Tyr Ile Arg Ala Glu Val Glu Asp Asn Ile Met
1745                1750                1755                1760

Val Thr Phe Lys Asn Gln Ala Ser Arg Pro Tyr Ser Phe Tyr Ser Ser
              1765                1770                1775

Leu Ile Ser Tyr Lys Glu Asp Gln Arg Gly Glu Glu Pro Arg Arg Asn
              1780                1785                1790

Phe Val Lys Pro Asn Glu Thr Lys Ile Tyr Phe Trp Lys Val Gln His
              1795                1800                1805

His Met Ala Pro Thr Glu Asp Glu Phe Asp Cys Lys Ala Trp Ala Tyr
              1810                1815                1820

Phe Ser Asp Val Asp Leu Glu Arg Asp Met His Ser Gly Leu Ile Gly
1825                1830                1835                1840

Pro Leu Leu Ile Cys His Ala Asn Thr Leu Asn Pro Ala His Gly Arg
              1845                1850                1855

Gln Val Ser Val Gln Glu Phe Ala Leu Leu Phe Thr Ile Phe Asp Glu
              1860                1865                1870

Thr Lys Ser Trp Tyr Phe Thr Glu Asn Val Lys Arg Asn Cys Lys Thr
              1875                1880                1885

Pro Cys Asn Phe Gln Met Glu Asp Pro Thr Leu Lys Glu Asn Tyr Arg
              1890                1895                1900

Phe His Ala Ile Asn Gly Tyr Val Met Asp Thr Leu Pro Gly Leu Val
1905                1910                1915                1920

Met Ala Gln Asp Gln Arg Ile Arg Trp Tyr Leu Leu Ser Met Gly Asn
              1925                1930                1935

Asn Glu Asn Ile Gln Ser Ile His Phe Ser Gly His Val Phe Thr Val
              1940                1945                1950

Arg Lys Lys Glu Glu Tyr Lys Met Ala Val Tyr Asn Leu Tyr Pro Gly
              1955                1960                1965

Val Phe Glu Thr Leu Glu Met Ile Pro Ser Arg Ala Gly Ile Trp Arg
              1970                1975                1980

Val Glu Cys Leu Ile Gly Glu His Leu Gln Ala Gly Met Ser Thr Leu
1985                1990                1995                2000

Phe Leu Val Tyr Ser Lys Gln Cys Gln Ile Pro Leu Gly Met Ala Ser
              2005                2010                2015

Gly Ser Ile Arg Asp Phe Gln Ile Thr Ala Ser Gly His Tyr Gly Gln
              2020                2025                2030

Trp Ala Pro Asn Leu Ala Arg Leu His Tyr Ser Gly Ser Ile Asn Ala
              2035                2040                2045

Trp Ser Thr Lys Glu Pro Phe Ser Trp Ile Lys Val Asp Leu Leu Ala
2050                2055                2060

Pro Met Ile Val His Gly Ile Lys Thr Gln Gly Ala Arg Gln Lys Phe

| | | | |
|---|---|---|---|
| 2065 | 2070 | 2075 | 2080 |

Ser Ser Leu Tyr Ile Ser Gln Phe Ile Ile Met Tyr Ser Leu Asp Gly
                    2085              2090              2095

Lys Lys Trp Leu Ser Tyr Gln Gly Asn Ser Thr Gly Thr Leu Met Val
            2100              2105              2110

Phe Phe Gly Asn Val Asp Ser Ser Gly Ile Lys His Asn Ser Phe Asn
        2115              2120              2125

Pro Pro Ile Ile Ala Arg Tyr Ile Arg Leu His Pro Thr His Ser Ser
    2130              2135              2140

Ile Arg Ser Thr Leu Arg Met Glu Leu Met Gly Cys Asp Leu Asn Ser
2145              2150              2155                      2160

Cys Ser Ile Pro Leu Gly Met Glu Ser Lys Val Ile Ser Asp Thr Gln
                2165              2170              2175

Ile Thr Ala Ser Ser Tyr Phe Thr Asn Met Phe Ala Thr Trp Ser Pro
            2180              2185              2190

Ser Gln Ala Arg Leu His Leu Gln Gly Arg Thr Asn Ala Trp Arg Pro
        2195              2200              2205

Gln Val Asn Asp Pro Lys Gln Trp Leu Gln Val Asp Leu Gln Lys Thr
    2210              2215              2220

Met Lys Val Thr Gly Ile Ile Thr Gln Gly Val Lys Ser Leu Phe Thr
2225              2230              2235                      2240

Ser Met Phe Val Lys Glu Phe Leu Ile Ser Ser Ser Gln Asp Gly His
                2245              2250              2255

His Trp Thr Gln Ile Leu Tyr Asn Gly Lys Val Lys Val Phe Gln Gly
            2260              2265              2270

Asn Gln Asp Ser Ser Thr Pro Met Met Asn Ser Leu Asp Pro Pro Leu
        2275              2280              2285

Leu Thr Arg Tyr Leu Arg Ile His Pro Gln Ile Trp Glu His Gln Ile
    2290              2295              2300

Ala Leu Arg Leu Glu Ile Leu Gly Cys Glu Ala Gln Gln Gln Tyr
2305              2310              2315

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:9:

CCTTCCTTTA TCCAAATACG TAGATCAAGA GGAAATTGAC    40

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:10:

GTAGCGTTGC CAAGAAGCAC CCTAAGACG                29

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:11:

GAAGAGTAGT ACGAGTTATT TCTCTGGGTT CAATGAC                37

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:12:

CCTTTATCCA AATACGTAGC GTTTGCCAAG AAG                33

---

We claim:

1. A purified hybrid factor VIII molecule comprising non-human mammalian and human amino acid sequences, wherein the molecule has procoagulant activity in an in vitro coagulation assay and wherein the molecule is selected from the groups consisting of human factor VIII protein comprising one or more non-porcine, non-human mammalian A1, A2, B, A3, C1 or C2 domains substituted for the corresponding human factor VIII domains;

non-porcine, non-human mammalian factor VIII protein comprising one or more human A1, A2, B, A3, C1 or C2 domains substituted for the corresponding non-porcine, non-human mammalian factor VIII domains;

human factor VIII protein comprising one or more porcine A1, B, A3, C1, or C2 domains substituted for the corresponding human factor VIII domains; and porcine factor VIII protein comprising one or more human A1, B, A3, C1, or C2 domains substituted for the corresponding human factor VIII domains.

2. The molecule of claim 1, wherein the hybrid factor VIII has a specific activity greater than 20,000 $U/A_{280}$ protein in aqueous solution when human plasma is used as the standard in a one-stage coagulation assay.

3. The molecule of claim 1, wherein the corresponding domain to be substituted by the domain of the other species includes an antigenic site that reacts with antibodies to factor VIII that inhibit coagulation activity, and wherein the hybrid factor VIII is less immunoreactive than human factor VIII with the inhibitory antibodies to factor VIII.

4. The molecule of claim 1, wherein the hybrid factor VIII is useful in treating human patients having antibodies to factor VIII that inhibit coagulation activity.

5. The molecule of claim 1, wherein the hybrid factor VIII is combined with a pharmaceutically acceptable carrier.

6. The molecule of claim 5, wherein the carrier is selected from the group consisting of stabilizing agents and delivery vehicles.

7. The molecule of claim 6, wherein the stabilizing agents are selected from the group consisting of proteins and polysaccharides.

8. The molecule of claim 6, further comprising clotting factors selected from the group consisting of von Willebrand factor, vitamin K dependent clotting factors, and coagulant tissue factor.

9. The molecule of claim 6, wherein the delivery vehicles are liposomes.

10. The molecule of claim 1 further comprising reagents for determining the presence of antibodies in a sample that are immunoreactive with the molecule.

11. The hybrid factor VIII molecule of claim 1, wherein the non-porcine, non-human mammalian domain substituted for the corresponding human factor VIII domain is the A2 domain.

12. The hybrid factor VIII molecule of claim 1, wherein the non-porcine, non-human mammalian domain to be substituted for the human domain is murine.

13. The molecule of claim 1, wherein the hybrid factor VIII molecule lacks all or part of the B domain.

14. A method of preparing purified hybrid factor VIII, wherein the hybrid factor VIII comprises non-porcine, non-human mammalian and human amino acid sequences, comprising the steps of transforming a host cell with expressible recombinant DNA encoding factor VIII comprising domains selected from the group consisting of A1, A2, B, A3, C1 and C2 domains in the light chain and heavy chain subunits of non-porcine, non-human mammalian and human factor VIII, expressing said DNA in said host cell, and purifying hybrid factor VIII that comprises non-porcine, non-human mammalian and human amino acid sequences thereby preparing said purified hybrid factor VIII.

15. The method of claim 14, wherein the domain is A2.

16. The method of claim 14, wherein the non-porcine, non-human mammalian domain is murine.

17. The method of claim 14, further comprising the step of deleting all or part of the B domain to make a hybrid B-domainless factor VIII.

18. A method of preparing hybrid factor VIII DNA wherein the DNA comprises a sequence encoding a non-human mammalian amino acid sequence and a human amino acid sequence comprising replacing a segment of DNA encoding human factor VII as shown in SEQ ID NO:2 with the corresponding sequence of a non-human mammalian DNA wherein the segment to be replaced corresponds to amino acid sequence selected from the group consisting of $NH_2$-terminal 63 percent of the human A2 domain and the amino acid sequence between amino acids 373 and 536, of human factor VIII.

19. The method of claim 18, wherein the non-human mammalian amino acid sequence is murine or porcine.

20. The method of claim 18, further comprising the step of deleting all or part of the B domain to make a hybrid B-domainless factor VIII.

21. A hybrid factor VIII molecule comprising non-human mammalian and human amino acid sequences wherein the molecule has procoagulant activity in an in vitro coagulation assay wherein a segment of the amino acid sequence of human factor VIII as set forth in SEQ ID NO:2 is replaced by a corresponding segment of non-human mammalian factor VIII, the segment being replaced being selected from the group consisting of $NH_2$-terminal 63 percent of the A2 domain of human factor VIII and amino acid sequence between amino acids 373 and 536 of human factor VIII.

22. The hybrid factor VIII molecule of claim 21 having reduced immunoreactivity to antibodies directed to human factor VIII.

23. The hybrid factor VIII of claim 21 lacking part or all of the B-domain.

* * * * *

UNITED STATES PATENT AND TRADEMARK OFFICE
CERTIFICATE OF CORRECTION

PATENT NO.   : 5,663,060

DATED        : September 2, 1997

INVENTOR(S)  : Lollar et al.

It is certified that error appears in the above-identified patent and that said Letters Patent is hereby corrected as shown below:

In Col. 18, line 43, replace "10.02M Hepes" with --0.02M Hepes--.

In Col. 18, line 44, replace "10-6M CaCl$_2$" with --0.6M CaCl$_2$--.

In Col. 22, line 63, replace "*Nature* 342-1347," with --*Nature* 342-347,--.

Signed and Sealed this

First Day of September, 1998

Attest:

BRUCE LEHMAN

Attesting Officer

Commissioner of Patents and Trademarks